United States Patent
Davis (10) Patent No.: US 8,287,919 B2
(45) Date of Patent: Oct. 16, 2012

(54) **LOW ENVIRONMENTAL IMPACT PESTICIDE MADE FROM "GRAS" INGREDIENTS FOR USE AGAINST *COQUI* FROGS AND OTHER SPECIES**

(76) Inventor: David P. Davis, Kurtistown, HI (US)

( * ) Notice: Subject to any disclaimer, the term of this patent is extended or adjusted under 35 U.S.C. 154(b) by 0 days.

(21) Appl. No.: 12/763,392

(22) Filed: Apr. 20, 2010

(65) Prior Publication Data

US 2010/0273885 A1    Oct. 28, 2010

Related U.S. Application Data

(60) Provisional application No. 61/170,987, filed on Apr. 20, 2009.

(51) Int. Cl.
*A01N 59/06* (2006.01)
*A61K 33/06* (2006.01)

(52) U.S. Cl. .................................................. 424/696
(58) Field of Classification Search ................ 424/696
See application file for complete search history.

(56) References Cited

U.S. PATENT DOCUMENTS

| | | | |
|---|---|---|---|
| 6,436,891 B1 | 8/2002 | Kemp et al. | |
| 6,572,908 B2 | 6/2003 | Kemp et al. | |
| 6,808,730 B2 | 10/2004 | Kemp et al. | |
| 6,881,424 B1 | 4/2005 | Kemp et al. | |
| 6,902,753 B1 | 6/2005 | Kemp et al. | |
| 7,323,436 B2 | 1/2008 | Kemp et al. | |
| 2005/0215458 A1* | 9/2005 | Lalum et al. ................ | 510/438 |

OTHER PUBLICATIONS

Hutchinson (MS Thesis in Biomedical Sciences, Dec. 2003, University of Hawaii Library).*
Meat Industry Services ( Acidic Calcium Sulphate properties, updated Jun. 2006).*
(2004. Dermal toxicity of citric acid based pesticide to introduced *Eleutherodactylus* frogs in Hawaii. QA 922 Final Report. USA, APHIS, Wildlife Services, National Wildlife Research Center. Hilo, HI, 12pp).*
'Homeowners guide to Stpopping the spread of *coqui* Frogs on Maui, Maui invasive Species Committee, Paia, HI. May 2003.
Product Safety Assessment Data Sheet of Propionic Acid, From Dow Chemical, printed, 2008.

* cited by examiner

*Primary Examiner* — Benjamin Packard
(74) *Attorney, Agent, or Firm* — Craig Conrad (57) ABSTRACT

The current invention involves compositions and methods for killing various soft-bodied animals of interest (more specifically, Coqui frogs and Coqui frog eggs are targeted) with a low pH adjusted pesticide. The method involves contacting the soft-bodied animal of interest with the low pH adjusted pesticide, wherein the pesticide is a propionic acid composition, a citric acid composition, an Acidic Calcium Sulfate (ACS) composition, or combination thereof. The preferred pesticide composition has a working concentration that is less than about 15% (w/v), and a pH less than about pH 2.5, which has a lethal effect on Coqui frogs, but is less phytotoxic than higher concentration pesticides. The method includes spraying any of the pH adjusted pesticides thoroughly an area inhabited by the soft-bodied animals of interest, which includes the under brush, under bushes, and typically any hiding places. On a large scale, the method contemplates filling various types of industrial spraying equipment with the pesticide and saturating entire pest inhabited areas.

6 Claims, 1 Drawing Sheet

LOW ENVIRONMENTAL IMPACT PESTICIDE MADE FROM "GRAS" INGREDIENTS FOR USE AGAINST *COQUI* FROGS AND OTHER SPECIES

RELATED APPLICATIONS

This application claims priority to U.S. Provisional Patent Application Ser. No. 61/170,987 titled "New Pesticide use for Propionic acid and/or its salts with or without the addition of ACS or ACS-P," filed on Apr. 20, 2009, having David Paul Davis, listed as inventor, the entire content of which is hereby incorporated by reference.

FEDERALLY SPONSORED RESEARCH

No federal funds were used in the development of the present invention.

JOINT RESEARCH AGREEMENTS

Not Applicable.

SEQUENCE LISTING

Not Applicable.

BACKGROUND

One aspect of this invention is an environmentally friendly, low phytotoxic acidic aqueous pesticide composition and a method for killing a soft-bodied animal (e.g. a Coqui frog; a Coqui frog egg; a tree frog, a cane toad, a slug, a nettle, a caterpillar, a nematode, an aphid, a spider mite, fruit fly larva, a varro mite and other soft bodied insects that are usually regarded as pests, or a combination thereof). More specifically, the acidic aqueous pesticide composition comprises: a low concentration of organic acid solution (less than 25%) and having a low pH (below about pH3). The active ingredient in the pesticide composition can be selected from acidic calcium sulfate (ACS), propionic acid, citric acid, or various functional equivalents including salts and esters, as described herein. The acidic aqueous pesticide composition of can further be formulated to comprise a sulfuric acid solution having a concentration below 10% (w/v) as a percentage of the aqueous pesticide composition. Additionally, the aqueous pesticide composition may further comprise a surfactant for the surface area of the aqueous pesticide composition on the soft bodied animal of interest wherein the surfactant is selected from: an ionic-, anionic-, zwitterionic-surfactant, or combination thereof.

Another aspect of the current invention is a method of killing a soft-bodied animal of interest with an acidic pesticide composition, the method comprising the steps of: locating the soft-bodied animal or locating an area where the soft-bodied animal resides; contacting the soft-bodied animal with one of the acidic pesticide compositions described herein. About 1 ml of this composition coming in contact with Coqui Frogs is lethal in less than about 15 minutes. This acidic pesticide composition represents a low environmental impact pesticide made from all GRAS ingredients also used in food processing and which are low in phytotoxicity.

The Coqui Frog: Hawaii's lush vegetation, warm temperatures and high humidity not only welcome human visitors but also indiscriminately provide a tropical paradise for the over 1,000 non-native plants, vertebrates, and invertebrates that have been accidentally introduced over the past 65 years. Some non-native species have become established at the expense of native species, competing for habitat and nutrient sources.

The Coqui frog, *Eleutherodactylus coqui*, was accidentally introduced into Hawaii from Puerto Rico in about 1988. Aside from being a major noise nuisance, the frogs pose a threat to Hawaii's island ecosystem. Coqui frogs have a voracious appetite that puts Hawaii's unique insects and spiders at risk directly. These frogs also compete with endemic birds and other native fauna that rely on insects for food. The frogs are quite adaptable to the different ecological zones and elevations in the state, which is demonstrated by populations being found from sea level to 4,000 feet elevations. Scientists are also concerned that an established coqui frog population may serve as a readily available food source if (or when) brown tree snakes are accidentally introduced in Hawaii.

Coqui frogs belong to a genus of frogs that do not have a tadpole stage and therefore do not require a body of water to reproduce. Instead, the female lays the eggs on damp moss or leaf litter, or inside a rolled or folded leaf, and the eggs are brooded by the male, who keeps them moist until they hatch.

At first, the eggs look white to off-white and opaque, about the size of large tapioca pearls. As they mature, the eggs enlarge, darken and become transparent, resembling papaya seeds, with the frog embryo visible inside. When the tiny froglets hatch in 14-17 days, they are about 5 mm long.

In its native Puerto Rico, the female coqui frog usually lays a cluster or clutch of 34-75 eggs four to six times a year. Under laboratory conditions in Hawaii, mating pairs can produce a clutch every 2½ weeks without loss of fertility, which results in about 26 clutches per year, or more than 1,400 eggs per female per year. It takes about 8 months for froglets to mature, and adult coqui frogs may live as long as 4-6 years.

Coqui populations have exploded in Hawaii over the last 15 years from presumably a single infestation to over 200 infestations on the Big Island alone. These frogs are also present on Maui (e.g. 40 or more infestations), Oahu (5 sites) and most recently on Kaua'i (1 site, which was the subject of an eradication effort with citric acid). In their native Puerto Rico, a 20×20 m plot averages about 40 reproductively mature adults (note: this number excludes juveniles). In contrast, a 20×20 m plot on the big island contains >200 reproductively mature adults. One reason for the population explosion is believed to be the lack of natural predators (e.g. owls, snakes, tarantulas, scorpions) in Hawaii.

Respiration and Circulation in Frog Skin. Although not wanting to be bound by theory, many of the methods described below take advantage of the skin of a frog being permeable to oxygen and carbon dioxide, as well as to water. Briefly, there are a number of blood vessels near the surface of the skin. When a frog is underwater, oxygen is transmitted through the skin directly into the bloodstream. On land, adult frogs can use their lungs to breathe, but the chest muscles are not involved in respiration, and there are no ribs or diaphragm to support breathing. Frogs breathe by taking air in through the nostrils (which often have valves which close when the frog is submerged), causing the throat to puff out, then compressing the floor of the mouth, which forces the air into the lungs. In August 2007 an aquatic frog named *Barbourula kalimantanensis* was discovered in a remote part of Indonesia. The Bornean Flat-headed Frog (*B. kalimantanensis*) is the first species of frog known to science without lungs.

Frogs are known for their three-chambered heart, which they share with all tetrapods except birds, crocodilians and mammals. In the three-chambered heart, oxygenated blood from the lungs and de-oxygenated blood from the respiring tissues enter by separate atria, and are directed via a spiral valve to the appropriate vessel—aorta for oxygenated blood and pulmonary artery for deoxygenated blood. This special structure is believed to be essential to keeping the mixing of the two types of blood to a minimum, which enables frogs to have higher metabolic rates, and to be more active than otherwise.

Some species of frog have remarkable adaptations that allow them to survive in oxygen deficient water. The lake titicaca frog (*Telmatobius culeus*) is one such species and to survive in the poorly oxygenated waters of Lake Titicaca it has incredibly wrinkly skin that increases its surface area of the skin to enhance gas exchange. This frog will also do 'push-ups' on the lakebed to increase the flow of water around its body.

The Coqui frog has demonstrated its ability to quickly adapt to Hawaii's ecosystem by an unprecedented population explosion that can reach eight to ten thousand frogs per square acre. Such a mega-group of frogs is estimated to eat about 47,500 insects per night. The absence of natural predators and its noisy mating behavior have made the Coqui frog the target of government and community eradication efforts. There are many different methods currently used to control and eradicate the Coqui frog in Hawaii. Many of the eradication methods take advantage of the frogs ability to breath through its skin. Some methods are described below, however, one of ordinary skill in the art will realize that the methods of population control and/or eradication described herein are by no means all-inclusive.

Methods of Pest Population Control

The primary control methods include but are not limited to chemical sprays, hot water sprays, hand capture and trapping, and environmental management. For lack of an acceptable and affordable commercially available pesticide, there are many environmentally hazardous substances that are being applied to infested areas by desperate residents seeking relief form the noisy calling of the Coqui frog. Environmental management is preferred by those who are against the application of chemicals and who are willing to clear away the vegetation and underbrush in which the Coqui frog hides during the day and may lay its eggs. Although labor intensive and in some cases detrimental to the horticultural diversity and appeal of the landscape, environmental management can be very effective and is especially useful in developing frog free zones around commercial nurseries and public buildings. If effective protocols are used in commercial nurseries to assure transported plants are free from Coqui frogs, infestations of this species to different parts of the island will continue.

Hand Capture.

The Hawaii Department of Agriculture personnel have devised a tool consisting of a length of plastic tubing (e.g. fluorescent light tube protective sheath that is sold at hardware stores in 8-ft lengths) cut at an angle, with a plastic bag taped over one end. Place the open end of the tube over the frog, and the frog will invariably hop into the tube and can be tipped into the bag. Once the frogs have been captured, freezing can effectively euthanize them. One of the problems with the capture approach is the amount of time required to capture and euthanize the large numbers of frogs needed to reduce the infestation population. It is also very difficult for the average person to find and capture the frogs, which are experts at calling from protected and hidden locations. Additionally, the capture and euthanize method does little to prevent clutches of frog eggs from hatching shortly after the mature adults have been captured.

Another control method is to make a lure or trap out of PVC or bamboo pipe. In order to accent the capture and euthanize methods, lures can be utilized to entice frogs into laying eggs in the lure wherein the frogs and eggs can be eradicated together. For example, Refugia Lures made from either bamboo or PVC pipe provides retreat and nesting site for Coqui frogs. These lures may comprise a ¾- to 1-inch inner diameter and 8-10 inches in length of cylindrical bamboo or PVC pipe, which is closed on one end. A 1-inch drilled hole along the side of the tube, about 4 inches from the closed end, serves as an entrance/exit for the frog. These lures can be preferred refuge sites or homes for the frogs when they are attached 3 to 5 ft above the ground on trees or stakes in infested areas. Lure efficiency in tests at Lava Tree State Monument Park has been estimated to be around 28% to 30%.

Although the frogs can freely come and go from the lures, they rarely try to escape, especially when tending a clutch of eggs, and can be easily captured. These devices are meant to LURE the frogs into using either the bamboo or PVC shelter instead of plants, trees or rock walls to lay their eggs (like a birdhouse). Because the frogs are not "trapped", the lures must be checked during the day at least every 2 weeks because eggs hatch in about 14 days. Using the lure capture methods, one of ordinary skill in the art can remove any adults that have taken up residence, as well as any eggs. Captured frogs and eggs may be destroyed by placing them in a zip lock bag or container and applying any one of a number of treatments including, but not limited to: filling the container with hot, soapy water (at least 113° F. for 3 min.); freezing the frogs/eggs for at least 3 hours; or thoroughly frogs/eggs with chemicals known to kill frogs.

By destroying the egg clutch as well as the adult frog, one can reduce the population of Coqui frogs in the area, but will not eliminate an established population of Coqui frogs. Additionally, the lure methods do not work well in a densely vegetated area having ample natural nesting sites. However, one major problem with the lure, capture and euthanize method is assuring that the frogs and frog eggs are dead before disposal because this method has been shown to accidentally lead to frog infestations at dump sites. Moreover, the hand-capture and lure method will only serve to make minimal reductions in any frog population and are most useful as a backyard approach. Hot water sprays or rinses are primarily used in nursery or commercial grower settings where the procedure can be accomplished in a controlled setting.

Caffeine.

Caffeine is found in many plant species, where it acts as a natural pesticide, with high caffeine levels being observed in seedlings that are still developing foliages, but are lacking mechanical protection. Caffeine has been shown to paralyze and kill certain insects feeding upon the plant. High caffeine levels have also been found in the surrounding soil of coffee bean seedlings. Therefore, it is understood that caffeine has a natural function as both a natural pesticide and an inhibitor of seed germination of other nearby coffee seedlings, thus giving it a better chance of survival. Based on the natural pesticide properties, the use of caffeine to control frogs has been utilized in the past. However, one of the major drawbacks for the large scale use of caffeine to control frog populations is the high cost.

Pyrenone.

Pyrethrins are natural organic compounds that have potent insecticidal activity. Pyrethrin I and pyrethrin II are structurally related esters with a cyclopropane core. They differ by the oxidation state of one carbon. They are viscous liquids that oxidize to become inactivated. They are non-persistent, being biodegradable, and break down on exposure to light or oxygen. The chemical structure of pyrethrins is the basis for a variety of synthetic insecticides called pyrethroids such as bifenthrin, permethrin and cypermethrin. Pyrenone, a pyrethrin (Bayer AG), was tested on Coqui frog eggs. Egg clusters or clutches (at least 4 days old) were cleared of dead or infertile eggs and dissected into two masses; one half was treated and the other served as untreated control. A solution of Pyrenone (14 oz/100 gal) was sprayed over the egg masses, which were observed until hatching. Nearly 92% of the eggs that were treated with Pyrenone hatched, compared to 97% among the untreated eggs. For eggs at the ages tested (4-7 days after being laid), Pyrenone does not seem to provide effective control.

Hydrated Lime.

In 2005 hydrated lime was approved for use against the Coqui as an emergency local use pesticide, however it was very hazardous to use and under strict controls. The use permit of hydrated lime expired in 2008, and although the state of Hawaii is considering asking for renewal for commercial growers only they are concerned about the environmental hazard potential. Additionally, this method of eradicating frogs leaves an unaesthetic white coating on plants, clogs sprayers, and is not entirely effective.

Spray Citric Acid Solution.

Taking advantage of the frog's unique respiratory and circulatory system in the skin, commercially available organic weak acids have been sprayed onto frog infested plants to kill Coqui frog-eggs, -juveniles, and -mature adults. Citric acid is a weak organic acid, and it is a natural preservative and is also used to add an acidic, or sour, taste to foods and soft drinks In biochemistry, it is important as an intermediate in the citric acid cycle and therefore occurs in the metabolism of virtually all living things.

Citric acid is an exempt active ingredient per 40 CFR 152.25 (g), and according to EPA for ingredients on List 4A, no consideration needs to be given to its effect on non-target species and or ground water. Only a few other organic acids like propionic acid and its salts as mentioned below are on List 4B, and are similarly permitted with an exempt status. As such, citric acid can also be used as an environmentally benign cleaning agent. In fact, lemons and limes have particularly high concentrations of the acid; it can constitute as much as 8% of the dry weight of these fruits (about 47 g/L in the juices). The concentrations of citric acid in citrus fruits ranging from 0.005 mol/L for oranges and grapefruits to 0.30 mol/L in lemons and limes. Because citric acid is a common food additive and is considered safe for environmental use by the EPA, it has been used in efforts to control the Coqui frog population in Hawaii. More specifically, citric acid (anhydrous, or dry powder) can be obtained in 50 lb bags or in repackaged 5 and 10 lb bags from chemical or garden supply stores. Typically, the citric acid dry powder must be mixed with water to make a 16% (w/v) solution, which is about 1.3 lb citric acid per 1 gallon of water. Similar 16% citric acid solutions are also available in ready-to-use premixed solutions.

Unfortunately, frogs and frog eggs are only killed by direct contact with the spray and not by its residue. For maximum effectiveness, citric acid spraying should be done following removal of dense shrubs and dead foliage to increase contact with the frog. Additionally, the spray should be applied in the early evening after a drizzle or heavy rain, when frogs start to call, rather than during a dry period or drought when frogs remain hidden and call less frequently. Moderate to heavy rain will dilute and wash away sprayed citric acid, so a user should consult the weather forecast prior to spraying. It is also important to provide thorough coverage of plants with the citric acid solution, including undersides of leaves where frogs may be hiding. Spray or hand-capture frogs agitated by the citric acid that may jump out of the plants before they can find another hiding place. Frogs that are not directly contacted during citric acid spraying may retreat and males may refrain from calling for a few days before re-emerging. The user should repeatedly spray the citric acid solution every two-weeks (time it takes for eggs to hatch) and monitor for calling males up to one year because it takes time for hatchlings to mature.

One of the major drawbacks of liberally spraying citric acid every two weeks for eradication of frogs is the mild to severe damage caused to many plants. Citric acid sprayed on stressed, young, or growing plants can range from mild (e.g. leaf spotting or yellowing) to severe (e.g. death of the plant). To avoid damage to delicate plants or flowers, it is necessary to thoroughly rinse the treated plants with fresh water to completely remove citric acid residue about an hour after spraying. However, this may reduce the effectiveness of the frog eradication treatment. Phytotoxicity (chemical damage) of plants varies depending on exposure conditions. Pre-testing on a small section of a plant is always recommended. After spraying and/or rinsing, observe the section for a few days for discoloration before spraying a large number of plants or valuable plants. A simple phytotoxicity observation of common plants three days after treatment with citric acid (25%) can be rated as severe, moderate or light. For example, citric acid treatments on streptocarpus, calathea and eggplants have a severe phytotoxicity outcome. More specifically, most if not all the leaves turned black; flowers and leaves became bleached and recovery was slow. The guava plant, bromeliad, dendrobium orchid and leatherleaf fern have a moderate phytotoxicity rating with citric acid, wherein young leaves and new shoots burned; the outer edges of leaves burned and dropped; dark brown spots appeared where acid may have concentrated; and recovery of the plants were slow. However, in passion fruit and payaya, the phytotoxicity to citric acid was only slight, wherein the leaves were spotted white, or lesions formed on the trunk.

Superacids.

Because many frogs are able to absorb water and oxygen directly through the skin, especially around the pelvic area, citric acid has been used for this to kill frogs by disrupting respiration. Citric acid is not a formal pesticide and has the unwanted problem of being highly phytotoxic, even at relatively low concentrations (~16%). Although higher concentrations of organic acids are more effective killing agents for the Coqui frog, the higher concentrations of acid are also more phytotoxic to the surrounding environment. The present invention utilizes a highly acidic metalated organic acid that can be used alone or as an acidiluant, or pH adjuster for organic acids, wherein the resultant composition is more dilute and having a more acidic pH, which is capable of eradicating a frog population in an infested area, with a minimal phytotoxic effect. These highly acidic metalated organic acids are also know as superacids.

A superacid is an acid with acidity greater than that of 100% pure sulfuric acid, which has a Hammett acidity function ($H_0$) of −12. Commercially available superacids include trifluoromethanesulfonic acid ($CF_3SO_3H$), also known as triflic acid, and fluorosulfonic acid ($F_SO_3H$), both of which are about a thousand times stronger (i.e. have more negative $H_0$ values) than sulfuric acid. The strongest superacids are prepared by the combination of two components, a strong Lewis acid and a strong Brønsted acid.

The subject of U.S. Pat. No. 6,881,424 titled, "Highly Acidic Metalated Organic Acid," issued on Apr. 19, 2005, having Kemp et al., listed as inventors ("the Kemp '424 patent"), describes the production of some of these types of Acidic Calcium Sulfate (ACS) acids, the entire reference is hereby incorporated by reference. More specifically, the Kemp '424 patent teaches a highly acidic metalated organic acid composition and its preparation. The acidic composition can be prepared by mixing a monovalent or polyvalent cation and an organic acid in the presence of a strong oxyacid, wherein the resultant acidic composition is less corrosive to a ferrous metal than a solution of a mineral acid having the same acidic pH value as that of the acidic composition, and where in the acid composition is more biocidal than a mixture of the organic acid and a metal salt of the organic acid which mixture has the same acid normality value as that of the acidic composition. The acidic composition can be prepared by mixing at least one regenerating acid, at least one metal base, and at least one organic acid, wherein the amount of the regenerating acid is in excess of the equivalent amount of the metal base.

Additionally, the subject of U.S. Pat. No. 7,323,436 titled, "Adduct having an acidic solution of sparingly-soluble group IIA complexes," issued on Jan. 29, 2008 and having Kemp et al., listed as inventors ("the Kemp '436 patent"), describes an adduct having an acidic solution of sparingly-soluble Group IIA complexes. More specifically, the Kemp '436 patent teaches an adduct having an acidic solution of sparingly-soluble Group IIA complexes ("AGIIS") and at least one additive. The AGIIS can be prepared by mixing a mineral acid (such as sulfuric acid), and a Group IIA hydroxide (such as calcium hydroxide) or a Group IIA salt of a dibasic acid (such as calcium sulfate), or a mixture of the two Group IIA compounds, followed by removing the solid formed. The additives can be an alcohol, an organic acid or a surface-active agent. The composition has various uses, including cleaning, food production, decontamination, bioremediation, agricultural application, medical application, and detoxification of substances.

Although not wanting to be bound by theory, one of ordinary skill in the art will understand that the term "pH" in the present invention pertains mainly to the chemistry definition, wherein pH (short for potentiometric hydrogen ion concentration) is considered a measure of the acidity or basicity of a solution. Although not wanting to be bound by theory, pH approximates but is not equal to p[H], the negative logarithm (base 10) of the molar concentration of dissolved hydrogen ions (H+). Crudely, this matches the number of places behind the decimal point. For example 0.1 molar hydrochloric acid (a strong acid) should be near pH 1 and 0.0001 molar HCl should be near pH 4. Pure water is neutral, and can be considered either a very weak acid or a very weak base (center on the pH scale), giving it a pH of 7, or 0.0000001 M $H^+$. For an aqueous solution to have a higher pH, a base must be dissolved in it, which binds away many of these rare hydrogen ions. Hydrogen ions in water can be written simply as $H^+$ or as hydronium ($H_3O^+$) or higher species (e.g. $H_9O_4^+$) to account for solvation, but all describe the same entity.

Although not wanting to be bound by theory, the pH of a weak acid solution is calculated by means of an Initial-Change-Equilibrium Table ("ICE Table"). For acids with a pKa value greater than about 2, the formula to determine the approximated pH is as follows: [pH=½ ($pK_a$-log $c_0$)]. Accordingly, the pH of a citric acid solution can be approximated using pKa=3.15; MW=192 g/mol. Namely:

a 25% (w/v) solution (~1.34 M citric acid) pH=½ (3.15-log(1.34)=½ (3.15-(0.127))=pH=~1.5.

a 16% (w/v) solution (0.833 M citric acid) pH=½ (3.15-log(0.833)=½ (3.15-(-0.07))=pH=~1.61.

a 10% (w/v) solution (0.521 M citric acid) pH=½ (3.15-log(0.521)=½ (3.15-(-0.283))=pH=~1.99.

Similarly, the pH for dilutions of a less expensive weak organic acid (i.e. propionic acid) can be calculated using the pKa=~4.88; 74.08 g/mol; and density=0.99 g/ml. Namely, a 25% (w/v) solution (~3.37 M propionic acid) pH=½ (3.15-log(3.37)=½ (4.88-(0.52))=pH=~2.18.

a 16% (w/v) solution (~2.15 M propionic acid) pH=½ (3.15-log(2.15)=½ (4.88-(0.33))=pH=~2.28.

a 10% solution (~1.34 M propionic acid) pH=½ (4.88-log(1.34)=pH=½ (4.88-(0.127))=pH=~2.37.

Although not wanting to be bound by theory, the ability of such weak acids to kill frogs with ~100% efficacy occurs when the pH of the solution is less than about pH 2. In contrast, phytotoxicity of plants occurs with higher the concentration of the weak acid solution. As such, one object of the present invention is to utilize low concentration solutions of superacids alone, or as an organic acid pH adjuster to lower the pH of lower concentration weak acids without increasing its corrosive potential. Although not wanting to be bound by theory, the addition of a composition capable of lowering the pH of a weak acid solution without increasing its corrosive potential can be a valuable product in many fields such as medicine, biology, chemistry, food science, environmental science, oceanography and many others, including compositions capable of being used as a low phytotoxic pesticide for Coqui frogs and other species. Additionally, one skilled in the art appreciates that the low phytotoxic acidic pesticides and method used to kill soft-bodied animals can be a lower cost, and more effective alternative to many current methods used today without departing from the scope and spirit of the invention

SUMMARY

One aspect of the current application is an aqueous pesticide composition that comprises a propionic acid solution having a concentration in the range of about 5.0% to 25%. The pH of this composition is in the range of pH about 0.5 to about pH 3.0. The pH of the proprionic acid pesticide composition can be adjusted to within a range of pH 0.5 to pH 3.0 using an acidic calcium sulfate (ACS) solution or a sulfuric acid solution. The pH adjusted propionic compositions can be a liquid or a solid and both are lethal to Coqui frogs and Coqui frog eggs when contacted. These compositions may have mild phytotoxic effects on plants. In one embodiment, the aqueous pesticide composition has a proprionic acid concentration in the range of 5% to 15%, and a pH in the range of pH 0.8 to pH 2.5. In a preferred embodiment, the aqueous pesticide composition has a proprionic acid concentration in the range of 8% to 12%, and the pH in the range of pH 1.0 to pH 2.0. In a most preferred embodiment, the aqueous pesticide composition has a proprionic acid concentration of about 12% and the pH in the range of about pH 1.5. A surfactant can be added to the proprionic acid composition to increases the surface area of the pesticide on the soft-bodied animal of interest.

A second aspect of the current application is an aqueous pesticide composition that comprises an Acidic Calcium Sulfate (ACS) solution having a concentration in the range of about 5.0% to 25%. The ACS composition can be a liquid or a solid and is lethal to Coqui frogs upon contact. These ACS compositions can be a liquid or a solid and both are lethal to Coqui frogs and Coqui frog eggs when contacted. These ACS compositions may have mild phytotoxic effects on plants. The pH of this ACS composition is in the range of pH about 0.5 to about pH 3.0. The pH of the ACS pesticide composition can be adjusted to within a range of pH 0.5 to pH 3.0 by adding a proprionic acid salt. In one embodiment, the aqueous pesticide composition has an ACS concentration in the range of 5% to 15%, and a pH in the range of pH 0.8 to pH 2.5. In a preferred embodiment, the aqueous pesticide composition has an ACS concentration in the range of 8% to 12%, and the pH in the range of pH 1.0 to pH 2.0. In a most preferred embodiment, the aqueous pesticide composition has a ACS concentration of about 11.5% and the pH in the range of about pH 1.5. A surfactant can be added to the ACS composition to increases the surface area of the pesticide on the soft-bodied animal of interest.

A third aspect of the current application is an aqueous pesticide composition that comprises a citric acid solution having a concentration in the range of about 5.0% to 25%. The pH of this composition is in the range of pH about 0.5 to about pH 3.0. The pH of the citric acid pesticide composition can be adjusted to within a range of pH 0.5 to pH 3.0 using an acidic calcium sulfate (ACS) solution or a sulfuric acid solution. The pH adjusted citric acid compositions can be a liquid or a solid and both are lethal to Coqui frogs and Coqui frog eggs when contacted. These compositions may have mild phytotoxic effects on plants. In one embodiment, the aqueous pesticide composition has a citric acid concentration in the range of 5% to 16%, and a pH in the range of pH 0.8 to pH 2.5. In a preferred embodiment, the aqueous pesticide composition has a citric acid concentration in the range of 8% to 12%, and the pH in the range of pH 1.0 to pH 2.0. In a most preferred embodiment, the aqueous pesticide composition has a citric acid concentration of about 12% and the pH in the range of about pH 1.5. A surfactant can be added to the citric acid composition to increases the surface area of the pesticide on the soft-bodied animal of interest. For example the soft bodied animals killed or repelled by the citric acid composition are tree frogs, cane toads, ants, termites, slugs, nettle and other caterpillars, nematodes, aphids, spider mites, fruit fly larva, varro mites of the honey bee, and other soft bodied insects that are usually regarded as pests.

A fourth aspect of the current invention is a method of killing a soft-bodied animal of interest with a pesticide. The method involves contacting the soft-bodied animal with the pesticide, wherein the pesticide is a propionic acid composition, a citric acid composition, or an ACS composition having a concentration in the range of 5.0% to 15%, and a pH in the range of pH 0.5 to pH 3.0. Part of the method includes spraying any of the previously mentioned pH adjusted pesticides an area inhabited by the soft-bodied animals of interest. In a specific embodiment, the soft-bodied animals of interest comprise Coqui frogs and Coqui frog eggs. Additionally, other soft bodied animals such as tree frogs, cane toads, ants, termites, slugs, nettle and other caterpillars, nematodes, aphids, spider mites, fruit fly larva, varro mites of the honey bee, and other soft bodied insects that are usually regarded as pests are also killed by this method. One portion of this method may include using lures or traps to encourage the soft-bodied animals of interest to inhabit the traps or lures prior to spraying the pesticide in small confined, yet specific areas. On a larger scale, the method contemplates filling various types of spraying apparatus with the pesticide and saturating entire areas where the pests are located. More specifically for smaller areas less than about 100 sq meters, a hand sprayer or a garden sprayer with volumes less than about 10 liters will suffice. However, larger areas (i.e. acreage) may need larger sprayers such as: Mounted Sprayer-Semi Hydraulic; Trailed Sprayer; Mounted Sprayer With Hydraulic Boom; Trailed Sprayer With High Wheel; Trailed Sprayer High Wheel With Electronic Control Unit; Mounted Sprayer-Basic Type; Mounted Sprayer-Basic Type With Clean Water Tank; Garden Sprayer; High Pressure Diaphragm Pump; Power Sprayer With Electric or Fuel Powered Engine; Fertilizer Spreader; Inter row Rotary Cultivator; or functional equivalent thereof.

A fifth aspect of the current invention is a method of killing a soft-bodied animal of interest with a solid pesticide. The method involves contacting the soft-bodied animal with the pesticide, wherein the solid pesticide is a propionic acid composition, a citric acid composition, or an ACS composition having a concentration in the range of 5.0% to 15%, and a pH in the range of pH 0.5 to pH 3.0. Part of the method includes positioning the dried solid of any of the previously mentioned pH adjusted pesticides an area inhabited by the soft-bodied animals of interest. In a specific embodiment, the soft-bodied animals of interest comprise Coqui frogs and Coqui frog eggs. Additionally, other soft bodied animals such as tree frogs, cane toads, ants, termites, slugs, nettle and other caterpillars, nematodes, aphids, spider mites, fruit fly larva, varro mites of the honey bee, and other soft bodied insects that are usually regarded as pests are also killed by this method. However, before the solid pesticide can be placed, it must be made. The propionic acid composition, a citric acid composition, or an ACS composition having a concentration in the range of 5.0% to 15%, and a pH in the range of pH 0.5 to pH 3.0. can be mixed with a matrix, and allowed to dry. Some of the preferred matrix supports include: bentonite clay, montmorillonite clay, phyllosilicate, Florisil®, bayerite, pseudo-boehmite, alumina, silica gel, aluminum oxides, gibbisite, boehmite, porous glass, collagen, cellulose, etc.

BRIEF DESCRIPTION OF DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Terms:

Before describing the present invention in detail, it is to be understood that this invention is not limited to particular compositions or composition delivery systems, which may vary. One having ordinary skill in the art will understand that the terminology used herein is for the purpose of describing particular embodiments only, and is not intended to be limiting. In addition, before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive.

It must be noted that, as used in this specification and the appended claims, the singular forms "a," "an" and "the" include plural referents unless the context clearly dictates otherwise. Thus, for example, reference to "a pharmacologically active agent" includes a mixture of two or more such compounds, reference to "a base" includes mixtures of two or more bases, reference to "an acid" includes mixtures of two or more acids, and the like.

In describing and claiming the present invention, the following terminology will be used in accordance with the definitions set out below.

The terms "Active agent," "chemically active agent," "composition," and "pesticide" are typically used interchangeably herein to refer to compositions and drugs that may be useful as a preservative and additive for food and feed, as well as a pesticide for certain species. The terms also encompass chemically acceptable, chemically active derivatives and analogs of such compositions, including, but not limited to, salts, esters, amides, pro-drugs, active metabolites, inclusion complexes, analogs, and the like. Therefore, when the terms "active agent," "chemically active agent", or "pesticide" are used, it is to be understood that applicants intend to include the active composition per se as well as chemically acceptable, pharmaceutically acceptable, pharmacologically active salts, esters, amides, pro-drugs, active metabolites, inclusion complexes, analogs, etc., which are collectively referred to herein as "chemically or pharmaceutically acceptable derivatives," or "functional chemical derivatives thereof"

The term "ACS-P" as used in the present invention pertains to the by-product created during the manufacture of Acidic Calcium Sulfate ("ACS") according to the Mionix protocol. It consists of calcium sulfate saturated with sulfuric acid and its production is described below. Another way of describing ACS-P is the calcium salt of sulfuric acid that is highly saturated with sulfuric acid. When ACS 100, or 10N ACS, is manufactured the by-product has been called ACS-P 100. When ACS 50, or 5N ACS, is manufactured the by-product is called ACS-P 50.

The term "ACS" acidified calcium sulfate as used in the present invention pertains to acids, or acidic mixtures, used herein include acidic solution of sparingly-soluble Group IIA complexes ("AGIIS"); adduct having AGIIS, preferably it is the organic acid adduct, wherein the organic acid can be propionic acid, lactic acid, or both; sulfuric acid having calcium sulfate dissolved therein, the sulfuric acid can be concentrated sulfuric acid; highly acidic metalated organic acid ("HAMO"); highly acidic metalated mixture of inorganic acid ("HAMMIA"), and a mixture thereof. A first acid, or acidic mixture, is AGIIS. The acidic, or low pH, solution of sparingly-soluble Group IIA complexes ("AGIIS") may have a suspension of very fine particles, and the term "low pH" means the pH is below 7, in the acidic region. The AGIIS has a certain acid normality but does not have the same dehydrating behavior as a saturated calcium sulfate in sulfuric acid having the same normality. In other words, the AGIIS has a certain acid normality but does not char sucrose as readily as does a saturated solution of calcium sulfate in sulfuric acid having the same normality. Further, the AGIIS has low volatility at room temperature and pressure. It is less corrosive to a human skin than sulfuric acid saturated with calcium sulfate having the same acid normality. Not intending to be bound by the theory, it is believed that one embodiment of AGIIS comprises near-saturated, saturated, or super-saturated calcium, sulfate anions or variations thereof, and/or complex ions containing calcium, sulfates, and/or variations thereof.

The term "complex," as used herein, denotes a composition wherein individual constituents are associated. "Associated" means constituents are bound to one another either covalently or non-covalently, the latter as a result of hydrogen bonding or other inter-molecular forces. The constituents may be present in ionic, non-ionic, hydrated or other forms.

The term "surfactant," as used herein, refers to a blend of surface active agents that are usually organic amphiphilic compounds, meaning they contain both hydrophobic groups (their "tails") and hydrophilic groups (their "heads"). Therefore, they are soluble in both organic solvents and water. One of ordinary skill in the art understands that surfactants can be classified by the presence of formally charged groups in its head. A non-ionic surfactant has no charge groups in its head (e.g. tween, triton x-100, cetyl alcohol etc). The head of an ionic surfactant carries a net charge (e.g. Sodium dodecyl sulfate, CHAPS, benzalkonium chloride, etc). If the charge is negative, the surfactant is more specifically called anionic; if the charge is positive, it is called cationic. If a surfactant contains a head with two oppositely charged groups, it is termed zwitterionic. Some surfactants that may be useful for this invention include Perfluorooctanoate (PFOA or PFO); Perfluorooctanesulfonate (PFOS); Sodium dodecyl sulfate (SDS), ammonium lauryl sulfate, and other alkyl sulfate salts; Sodium laureth sulfate, also known as sodium lauryl ether sulfate (SLES); Alkyl benzene sulfonate; Soaps, or fatty acid salts; Cationic (based on quaternary ammonium cations); Cetyl trimethylammonium bromide (CTAB) a.k.a. hexadecyl trimethyl ammonium bromide, and other alkyltrimethylammonium salts; Cetylpyridinium chloride (CPC); Polyethoxylated tallow amine (POEA); Benzalkonium chloride (BAC); Benzethonium chloride (BZT); Zwitterionic (amphoteric); CHAPS (3-[(3-Cholamidopropyl)dimethylammonio]-1-propanesulfonate); Dodecyl betaine; Cocamidopropyl betaine; Coco ampho glycinate; Nonionic; Alkyl poly(ethylene oxide); Polysorbates: based on Polyoxyethylene Glycol, including the Tween series (ex.Tween 20, Tween 80), the Brij series]], the [[ex.Triton detergent[Triton]] series (ex.Triton X-100); Alkylphenol poly(ethylene oxide); Copolymers of poly(ethylene oxide) and poly(propylene oxide) (commercially called Poloxamers or Poloxamines); Alkyl polyglucosides; Octyl glucoside; Decyl maltoside; Fatty alcohols; Cetyl alcohol; Oleyl alcohol; Cocamide MEA, cocamide DEA; Dodecyl dimethylamine oxide The term "sprayer," as used herein, includes all types of sprayers for liquid and dry compositions. The sprayers contemplated include, but are not limited to: Hand Spray Bottles with volumes less than about 1 liter; Garden Sprayer with volumes less than about 10 liters; Mounted Sprayer-Semi Hydraulic; Trailed Sprayer; Mounted Sprayer With Hydraulic Boom; Trailed Sprayer With High Wheel; Trailed Sprayer High Wheel With Electronic Control Unit; Mounted Sprayer-Basic Type; Mounted Sprayer-Basic Type With Clean Water Tank; Garden Sprayer; High Pressure Diaphragm Pump; Power Sprayer With Electric or Fuel Powered Engine; Fertilizer Spreader; Interrow Rotary Cultivator. One of ordinary skill in the art will understand that any type of sprayer capable of spraying liquid or dry chemicals may be used for this invention.

The term "propionic acid," as used herein, denotes propionic acid, and other derivatives having a functional chemical equivalents having similar structures to $H(CH_2)_n COOH$ acid. Other names for propionic acid include: Carboxyethane, Ethanecarboxylic acid, Ethylformic acid, Metacetonic acid, Methyl acetic acid, Propanoic acid. Propionic acid has physical properties intermediate between those of the smaller carboxylic acids, formic and acetic acids, and the larger fatty acids. It is miscible with water, but can be removed from water by adding salt. As with acetic and formic acids, it consists of hydrogen bonded pairs of molecules both as the liquid and vapor. Propionic acid displays the general properties of carboxylic acids, wherein it can form amide, ester, anhydride, and chloride derivatives, all of which are included as functional equivalents. It can undergo alpha-halogenation with bromine in the presence of $PBr_3$ as catalyst (the HVZ reaction) to form $CH_3CHBrCOOH$. Currently the world's largest producer of propionic acid is BASF, with approximately 80 kt/a production capacity.

The term "acidity regulators", or "pH control agents" are generally denoted as food additives used to change or maintain pH (acidity or basicity) in a composition. They can be organic or mineral acids, bases, neutralizing agents, or buffering agents.

Preferred Embodiments

One aspect of the present invention pertains to a method employing an acidified pesticide to reduce, inhibit, or eradicate a large or small infestation that has resulted in a population growth of an invasive species of frog or other living soft-bodied organism, wherein the acidified pesticide has a minimum phytotoxic effect on local flora and fauna. Here an effective amount (i.e. in that the amount is sufficient to exert its lethal pesticide properties) of the composition is allowed to contact (e.g. such as by drenching, setting, laying, mixing, misting or spraying) the infestation area.

Although not wanting to be bound by theory, no absolute methods are available for completely eliminating invasive species in other environments without some adverse effects to some plants, animals, insects, fowls, reptiles, and the like, however, the acidified pesticide composition and method thereof do offer a economical and practical solution for reducing the population of an infestation area without significant damage to local flora and fauna. The compositions and methods of making and using acidic pesticides are described in the examples below:

EXAMPLES

The following examples are provided to further illustrate this invention and the manner in which it may be carried out. It will be understood by one of ordinary skill in the art, however, that the specific details given in the examples have been chosen for purposes of illustration only and not be construed as limiting the invention.

Example 1

Acids

Acidic Calcium Sulfate ("ACS").

A preferred method of preparing AGIIS involves mixing a mineral acid with a Group IIA hydroxide, or with a Group IIA salt of a dibasic acid, or with a mixture of the two Group IIA materials. In the mixing, a salt of Group IIA is also formed. Preferably, the starting Group IIA material or materials selected will give rise to, and form, the Group IIA salt or salts that are sparingly soluble in water. The preferred mineral acid is sulfuric acid, the preferred Group IIA hydroxide is calcium hydroxide, and the prefer Group IIA salt of a dibasic acid is calcium sulfate. Other examples of Group IIA salt include calcium oxide, calcium carbonate, and "calcium bicarbonate."

Thus, for example, AGIIS can be prepared by mixing or blending starting materials given in one of the following scheme with good reproducibility:

(1) $H_2SO_4$ and $Ca(OH)_2$;
(2) $H_2SO_4$, $Ca(OH)_2$, and $CaCO_3$;
(3) $H_2SO_4$, $Ca(OH)_2$, $CaCO_3$, and $CO_2$ (gas);
(4) $H_2SO_4$, $CaCO_3$, and $Ca(OH)_2$;
(5) $H_2SO_4$, $Ca(OH)_2$, and $CaSO_4$;
(6) $H_2SO_4$, $CaSO_4$, $CaCO_3$, and $Ca(OH)_2$;
(7) $H_2SO_4$, $CaSO_4$, $CaCO_3$, and $CO_2$ (gas); and
(8) $H_2SO_4$, $CaSO_4$, $CaCO_3$, $CO_2$ (gas), and $Ca(OH)_2$.

Preferably, AGIIS is prepared by mixing calcium hydroxide with concentrated sulfuric acid, with or without an optional Group IIA salt of a dibasic acid (such as calcium sulfate) added to the sulfuric acid. The optional calcium sulfate can be added to the concentrated sulfuric acid prior to the introduction of calcium hydroxide into the blending mixture. The addition of calcium sulfate to the concentrated sulfuric acid appears to reduce the amount of calcium hydroxide needed for the preparation of AGIIS. Other optional reactants include calcium carbonate and gaseous carbon dioxide being bubbled into the mixture. Regardless of the use of any optional reactants, it was found that the use of calcium hydroxide is desirable.

One preferred method of preparing AGIIS can be described briefly as: Concentrated sulfuric acid is added to chilled water (8°-12° C.) in the reaction vessel, then, with stirring, calcium sulfate is added to the acid in chilled water to give a mixture. Temperature control is paramount to this process. To this stirring mixture is then added slurry of calcium hydroxide in water. The solid formed from the mixture is then removed. This method involves the use of sulfuric acid, calcium sulfate, and calcium hydroxide, and it has several unexpected advantages. Firstly, this reaction is not violent and is not exceedingly exothermic. Besides being easy to control and easy to reproduce, this reaction uses ingredients each of which has been reviewed by the U.S. Food and Drug Administration ("U.S. FDA") and determined to be "generally recognized as safe" ("GRAS"). As such, each of these ingredients can be added directly to food, subject, of course, to certain limitations. Under proper concentration, each of these ingredients can be used as processing aids and in food contact applications. Their use is limited only by product suitability and Good Manufacturing Practices ("GMP"). The AGIIS so prepared is thus safe for animal consumption, safe for processing aids, and safe in food contact applications. Further, the AGIIS reduces biological contaminants in not only inhibiting the growth of, and killing, microorganisms but also destroying the toxins formed and generated by the microorganisms. The AGIIS formed can also preserve, or extend the shelf-life of, consumable products, be they plant, animal, pharmaceutical, or biological products. It also preserves or improves the organoleptic quality of a beverage, a plant product or an animal product. It also possesses certain healing and therapeutic properties.

The sulfuric acid used is usually 95-98% FCC Grade (about 35-37 N). The amount of concentrated sulfuric acid can range from about 0.05 M to about 18 M (about 0.1 N to about 36 N), preferably from about 1 M to about 5 M. It is application specific. The term "M" used denotes molar or moles per liter.

Normally, a slurry of finely ground calcium hydroxide suspended in water (about 50% of w/v) is the preferred way of introducing the calcium hydroxide, in increments, into a stirring solution of sulfuric acid, with or without the presence of calcium sulfate. Ordinarily, the reaction is carried out below 40° C., preferably below room temperature, and more preferably below 10° C. The time to add calcium hydroxide can range from about 1 hour to about 4 hours. The agitation speed can vary from about 600 to about 700 rpm or higher. After the mixing, the mixture is filtered through a 5 micron filter. The filtrate is then allowed to sit overnight and the fine sediment is removed by decantation.

The calcium hydroxide used is usually FCC Grade of about 98% purity. For every mole of concentrated acid, such as sulfuric acid, the amount, in mole, of calcium hydroxide used is application specific and ranges from about 0.1 to about 1.

The phosphoric acid used is usually from JT Baker of about 85-88%.

The calcium monohydrogen phosphate is usually of 98-99%; and the calcium phosphate ("the tribasic") is obtained from Mallinckrodt. Other phosphate salts used are all of reagent grade.

The optional calcium carbonate is normally FCC Grade having a purity of about 98%. When used with calcium hydroxide as described above, for every mole of concentrated acid, such as sulfuric acid, the amount, in mole, of calcium carbonate ranges from about 0.001 to about 0.2, depending on the amount of calcium hydroxide used.

The optional carbon dioxide is usually bubbled into the slurry containing calcium hydroxide at a speed of from about 1 to about 3 pounds pressure. The carbon dioxide is bubbled into the slurry for a period of from about 1 to about 3 hours. The slurry is then added to the reaction vessel containing the concentrated sulfuric acid.

Another optional ingredient is calcium sulfate, a Group IIA salt of a dibasic acid. Normally, dihydrated calcium sulfate is used. As used in this application, the phrase "calcium sulfate," or the formula "$CaSO_4$," means either anhydrous or hydrated calcium sulfate. The purity of calcium sulfate (dihydrate) used is usually 95-98% FCC Grade. The amount of calcium sulfate, in moles per liter of concentrated sulfuric acid ranges from about 0.005 to about 0.15, preferably from about 0.007 to about 0.07, and more preferably from about 0.007 to about 0.04. It is application specific.

In the event that $CaSO_4$ is used for the reaction by adding it to the solution of concentrated $H_2SO_4$, the amount of $CaSO_4$, in grams per liter of solution based on final volume, has the following relationship:

| Final AGIIS Acid Normality (N) | Amount of $CaSO_4$ in g/l |
|---|---|
| 1-5 | 5 |
| 6-10 | 4 |
| 11-15 | 3 |
| 16-20 | 2 |
| 21-36 | 1 |

The AGIIS obtained could have an acid normality range of from about 0.05 to about 31; the pH of lower than 0; boiling point of from about 100 to about 106° C.; freezing point of from about −8° C. to about 0° C. AGIIS obtained from using the reaction of $H_2SO_4/Ca(OH)_2/CaSO_4$ had the following analyses (average):

AGIIS With Final Acid Normality of 1.2 N, pH of −0.08

$H_3O^+$, 2.22%; Ca, 602 ppm; $SO_4$, 73560 ppm; K, 1.36 ppb; impurities of 19.68 ppm, and neither Na nor Mg was detected.

AGIIS With Final Acid Normality of about 29 N, pH of about −1.46

$H_3O^+$, 30.68%; Ca, 52.9 ppm; $SO_4$, 1422160 ppm; K, 38.02 ppb; and neither Na nor Mg was detected.

Aqueous solutions of other alkalis or bases, such as Group IA hydroxide solution or slurry and Group IIA hydroxide solution or slurry can be used. Groups IA and IIA refer to the two Groups in the periodical table. The use of Group IIA hydroxide is preferred. Preferably, the salts formed from using Group IIA hydroxides in the reaction are sparingly soluble in water. It is also preferable to use only Group IIA hydroxide as the base without the addition of Group IA hydroxide. After the reaction, the resultant concentrated acidic solution with a relatively low pH value, typically below pH 1, can then be diluted with de-ionized water to the desired pH value, such as pH of about 1 or about 1.8.

As discussed above, AGIIS has relatively less dehydrating properties (such as charring sucrose) as compared to the saturated solution of $CaSO_4$ in the same concentration of $H_2SO_4$. Further, the stability and non-corrosive nature of the AGIIS of the present invention can be illustrated by the fact that a person can put his or her hand into this solution with a pH of less than 0.5 and, yet, his or her hand suffers no irritation, and no injury. If, on the other hand, one places his or her hand into a solution of sulfuric acid of pH of less than 0.5, an irritation would occur within a relatively short span of time. A solution of 28 N of sulfuric acid saturated with calcium sulfate will cause chemical burn to a human skin after a few seconds of contact. In contrast, AGIIS solution of the same normality would not cause chemical burn to a human skin even after in contact for 5 minutes. The AGIIS does not seem to be corrosive when being brought in contact with the environmental protective covering of plants (cuticle) and animals (skin). AGIIS has low volatility at room temperature and pressure. Even as concentrated as 29N, the AGIIS has no odor, does not give off fumes in the air, and is not irritating to a human nose when one smells this concentrated solution.

A second acid, or acidic mixture, is an adduct having AGIIS, which comprises AGIIS and one more additives. The "additive" of the present invention appears to enhance, and also appears to be synergistic to, the effectiveness of the acidic composition of the present invention. Examples of the additive include alcohol, organic acid, periodic acid, and surfactant. The amount of additive added to the AGIIS varies depending on the desired final weight percent of the additive in the final adduct composition. The weight percent of additive needed for the adduct composition of the present invention can vary from about 0.01 to about 99.99, based on the total weight of the final adduct composition. The alcohol additive preferred for the present invention includes methanol, ethanol, 1-propanol, 2-propanol, and other lower alkyl alcohols.

Organic acid additive of the present invention includes carboxylic acid. A carboxylic acid is an organic compound containing the —COOH group, i.e., a carbonyl attached to a hydroxyl group. Preferred organic acids for the present invention include lactic acid, acetic acid, propionic acid, oxalic acid, sorbic acid, butyric acid, benzoic acid, glycolic acid, peracetic acid, and a mixture thereof.

A surfactant for the present invention is a surface-active agent. It is usually an organic compound consisting of two parts: One, a hydrophobic portion, usually including a long hydrocarbon chain; and two, a hydrophilic portion which renders the compound sufficiently soluble or dispersible in water or another polar solvent. Surfactants are usually classified into: (1) anionic, where the hydrophilic moiety of the molecule carries a negative charge; (2) cationic, where this moiety of the molecule carries a positive charge; and (3) non-ionic, which do not dissociate, but commonly derive their hydrophilic moiety from polyhydroxy or polyethoxy structures. Other surfactants include ampholytic and zwitterionic surfactants. A preferred surfactant for the present invention includes polysorbates (Tween 80).

Unless otherwise defined, the amount of each ingredient or component of the present invention is based on the weight percent of the final composition, usually the concentrate before further dilution to achieve the desired pH of about 1.8.

The AGIIS having a pH of about 1.8 is usually further diluted with water before applying to an animal product or a plant product.

A third acid, or acidic mixture, is highly acidic metalated organic acid ("HAMO"). The HAMO composition may have a suspension of very fine particles, and it has a monovalent or a polyvalent cation, an organic acid, and an anion of a regenerating acid, such as the anion of a strong oxyacid. The term "highly acidic" means the pH is in the acidic region, below at least about 4. HAMO of the present invention is less corrosive to a ferrous metal than a solution of a mineral acid having the same acidic pH value as that of the acidic composition. HAMO is also more biocidal than a mixture of the organic acid and a metal salt of the organic acid which mixture having the same acid normality value as that of the acidic composition.

Broadly, one way HAMO can be prepared is by mixing the following ingredients: (1) at least one regenerating acid; (2) at least one metal base; and (3) at least one organic acid, wherein the equivalent amount of the regenerating acid is in excess of the equivalent amount of the metal base. The equivalent amount of the metal base should be about equal to that of the organic acid. Instead of using a metal base and an organic acid, a metal salt of the organic acid can be used in place of the metal base and the organic acid. The insoluble solid is removed by any conventional method, such as sedimentation, filtration, or centrifugation.

Generally, HAMO can be prepared by blending or mixing the necessary ingredients in at least the following manners:

1. Regenerating acid+(metal base+organic acid);
2. Regenerating acid+(metal base+salt of organic acid);
3. (Regenerating acid+salt of organic acid)+base; and
4. Regenerating acid+salt of organic acid.

The parenthesis in the above scheme denotes "pre-mixing" the two ingredients recited in the parenthesis. Normally, the regenerating acid is added last to generate the HAMO. Although each of the reagents is listed as a single reagent, optionally, more than one single reagent, such as more than one regenerating acid or organic acid, can be used in the current invention. The number of equivalents of the regenerating acid must be larger than the number of equivalents of the metal base, or those of the metal salt of the organic acid. When the organic acid is an amino acid, which, by definition contains at least one amino group, then the number of equivalents of the regenerating acid must be larger than the total number of equivalents of the metal base, or metal salt of the organic acid, and the "base" amino group of the amino acid. Thus, the resultant highly acidic metalated organic acid is different from, and not, a buffer.

As used herein, a regenerating acid is an acid that will "re-generate" the organic acid from its salt. Examples of a regenerating acid include a strong binary acid, a strong oxyacid, and others. A binary acid is an acid in which protons are directly bound to a central atom, that is (central atom)-H. Examples of a binary acid include HF, HCl, HBr, $H_1$, $H_2S$ and $HN_3$. An oxyacid is an acid in which the acidic protons are bound to oxygen, which in turn is bound to a central atom, that is (central atom)-O—H. Examples of oxyacid include acids having Cl, Br, Cr, As, Ge, Te, P, B, As, I, S, Se, Sn, Te, N, Mo, W, or Mn as the central atom. Some examples include $H_2SO_4$, $HNO_3$, $H_2SeO_4$, $HClO_4$, $H_3PO_4$, and $HMnO_4$. Some of the acids (e.g. $HMnO_4$) cannot actually be isolated as such, but occur only in the form of their dilute solutions, anions, and salts. A "strong oxyacid" is an oxyacid which at a concentration of 1 molar in water gives a concentration of $H_3O^+$ greater than about 0.8 molar. The regenerating acid can also be an acidic solution of sparingly-soluble Group IIA complexes ("AGIIS").

A fourth acid, or acidic mixture, is a highly acidic metalated mixture of inorganic acids ("HAMMIA"). The composition has an acidic pH, and can be isolated from a mixture prepared by mixing ingredients comprising a salt of phosphoric acid, and a preformed, or in-situ generated, solution or suspension of an acidic sparingly-soluble Group IIA complex ("AGIIS"), wherein the solution or suspension of AGIIS is in an amount sufficient to render the acidic pH of the composition to be less than about 2.

Each of the acid mixtures are the subject of the following U.S. patents and hereby incorporated by reference:

1. U.S. Pat. No. 7,323,436 titled: "Adduct having an acidic solution of sparingly-soluble group IIA complexes," issued to Kemp et al., on Jan. 29, 2008.
2. U.S. Pat. No. 6,902,753 titled: "Acidic solution of sparingly-soluble group IIA complexes," issued to Kemp et al., on Jun. 7, 2005.
3. U.S. Pat. No. 6,881,424 titled: "Highly acidic metalated organic acid," issued to Kemp et al., on Apr. 19, 2005.
4. U.S. Pat. No. 6,808,730 titled: "Highly acidic metalated organic acid as a food additive," issued to Kemp et al., on Oct. 26, 2004.
5. U.S. Pat. No. 6,572,908 titled: "Highly acidic metalated organic acid as a food additive," issued to Kemp et al., on Jun. 3, 2003.
6. U.S. Pat. No. 6,436,891 titled: "Adduct having an acidic solution of sparingly-soluble group IIA complexes," issued to Kemp et al., on Aug. 20, 2002.

One having ordinary skill in the art will recognize that Acidic Calcium Sulfate ("ACS") acids, as described above, are acid products that are found in nature, but can be manufactured in many ways. Such manufactured acids are considered to be functional chemical equivalents of the ACS acids described herein. For example, Hydrite Chemical Corporation (4031 Alvis Ct, Rocklin, Calif. 95677) manufactures a product for the Mionix Corporation called ACS 100 and ACS 50. These commercially manufactured products can be used to produce the product of this invention or as acid acidulant for different organic acids.

Although not wanting to be bound by theory. The ACS compositions are akin to citric acid as they appear on the EPA's list of inert ingredients, 4a or 4b, which can be used as a pesticide because of the minimal risk they pose to the environment. Propionic acid and its salts also appear on list 4b as does sulfuric acid, whereas calcium sulfate, dehydrate or hemihydrate, appears on list 4a. In fact, the use of ACS as an acidulant potentiates citric acid and makes it possible to use a lower concentration. ACS or another functional equivalent acidulant can also be used with citric acid or regenerate citric acid from its salt, which allows citric acid to be used at lower concentrations without decreasing its lethal potential to frogs.

Example 2

Agent Green™

This example shows how an approximate 12% by volume Acidic Calcium Sulfate can be used as a pH adjustor for agricultural uses. This solution can be marketed under a trade name of AGENT GREEN™, which is made from ingredients generally regarded as safe ("GRAS") by the FDA. Although not wanting to be bound by theory, Agent Green is a pH adjuster that increases the acidity and lowers the pH activity of water. It has many agricultural applications including but not limited to adjusting hydroponics growing medium, soil acidity, and sanitizing surfaces. One of the concentrated products can also be used to remove rust from iron and steel. It also has many of the same properties as citric acid, however it is less corrosive than citric acid. When properly diluted (pH 2.5) it can also be used as a plant nutrient to add calcium via foliar application.

Materials: Strong plastic or stainless steel scoop, stirring stick, 5 gal plastic bucket/container, scale with 10 lb capacity, pH meter or litmus sticks, goggles, plastic coveralls. (Be sure to use goggles and plastic coveralls to protect your eyes and cotton clothing when mixing concentrate.) Begin by adding 1.5-2 lbs of concentrate (calcium sulfate saturated with sulfuric acid) to one gallon of tap or catchment water. Always add product to water instead of adding water to product. Stir until well mixed. The ratio of 1.5 lbs of product per gallon of water will produce a pH of approximately 1.3. When product is mixed with water it immediately lowers the pH of the water while the white sediment quickly falls to the bottom of the mixing container. Depending upon your needs, you may obtain any acidity level or pH of water by adding more or less concentrates. (For example 2 lbs of concentrate per gallon of water will produce water with a pH below 1.0 whereas 1 lb of product per gallon of water will produce a pH of approximately 1.5-1.75. After mixing the product, pour off the low pH water leaving the white sediment in the container (also referred to by some as "white dirt") and safe for use as a soil amendment for plants that thrive in acidic soil. CAUTION: Agent Green concentrate is highly acidic as packaged in the container. The concentrate has little to no effect on the healthy skin of humans or animals; however it will damage cotton, cement, and certain metals. Use caution when mixing or applying concentrated solution of Agent Green. Use of the product with precipitant in suspension may clog a sprayer. If sprayer has metal parts rinse thoroughly after using. Applying a low pH (below 2.0 pH) to plants may result in harm to sensitive plants. Pre-test your plant for sensitivity. The active agent green has ACS in the range of about 3%-about 20%. The preferred active agent green has ACS in the range of about 5%-about 15%, and the most preferred active agent green has an ACS solution in the range in the about 10%-about 12%. The active agent green has a pH in the range of pH above 0 to about pH 3. The preferred active agent green has pH in the range of about pH 1-about pH 2.5, and the most preferred active agent green has a pH solution in the range about pH 1.5-about pH 2.0.

Minor irritation may occur if product is allowed to come into contact with eyes, cuts, or the mucus membranes of the nose and mouth. If an exposed area becomes irritated, rinse thoroughly with water until irritation subsides. Seek medical attention as needed. When mixing or applying concentrated product wear impervious protective clothing, including protective eyewear and use respirator or NIOSH recommended mask for applying chemicals when applying product as a fine mist. Avoid inhalation of product spray mist as irritation of the respiratory tract may result. Store with hazardous materials and keep out of reach of children.

Example 3

Agent Green™ Plant Finisher and Agriculture Acidulant (Solid)

AGENT GREEN™ plant finisher is a solid acidulant. This means it increases the acidic activity that results in compounds and dilute solutions capable of lowering the pH of water by adding hydrogen ion activity. It is useful for any agricultural application wherein the desired purpose is to lower the pH, or increase the acidity, of water. Application of acidic water to soil lowers the pH of the soil and facilitates plant absorption of nitrogen. This product contains added calcium and when applied to plant foliage as a spray it acts as a plant nutrient. When added to hydroponics growing medium or the water of fish or shrimp ponds this product will increase acidity and lower pH without adding any ingredients that are harmful.

Mix 1.5 lbs Acidic Calcium Sulfate ("ACS") solid product (calcium sulfate saturated with sulfuric acid) with one gallon of water. Stir well. After white precipitant falls to bottom of mixing container (takes about 5 to 10 minutes) decant or pour off clear liquid into a secondary container. The resulting liquid will be very acidic and have a pH of approximately 1.5. A litmus stick or pH meter can be use to monitor the pH activity, wherein more product or water can be added to reach the acidic strength desired. Use product as desired. If this product is used as a foliar spray be sure to use only the clear liquid as product may otherwise clog your sprayer. For best results, use product with an all plastic sprayer. If sprayer has metal parts rinse thoroughly after using. Spray clear liquid directly onto plant foliage or soil.

When mixed as directed, the resultant liquid has a pH of approximately 1.5 and is highly acidic having properties similar to those of citric acid however it is less corrosive than higher concentrations of citric acid having the pH lowered by the Agent Green™. In order to avoid possible harm to your plants test plant for sensitivity prior to application. If unsure of your plants sensitivity rinse the product off plant within thirty minutes of application. Hearty sun loving plants such as palms may tolerate the solution well whereas shade loving broad leaf or succulent plants such as bromeliads are more likely to be burned by the solution unless further dilutions are made by adding additional water. For sensitive plants try using one pound of product in two or up to five gallons of water as needed according to plant requirements. Heavy sprays may be used with hearty plants or application to the ground whereas a fine mist spray should be used with more sensitive plants. If plant shows signs of burns within about 12-48 hours of use dilute product further or discontinue use.

Minor irritation may occur if product is allowed to come into contact with eyes, cuts, or the mucus membranes of the nose and mouth. Wear impervious protective clothing, including eyewear, gloves, and boots as appropriate to prevent contact with eyes, skin and the mucus membranes of nose and mouth when mixing or applying this product. If an exposed area becomes irritated, rinse with water until irritation subsides. Seek medical attention as needed. Product will damage cotton clothing and most metals and cement. It does not damage polyester clothing.

The active agent green solid can be mixed to have a solution of ACS in the range of about 5%-about 20%. The preferred active agent green has ACS in the range of 8%-15%, and the most preferred active Agent Green™ has an ACS solution in the range of about 10%-about 12%. The active agent green has a pH in the range of pH above 0 to about pH 3. The preferred active Agent Green™ has pH in the range of about pH 1-about pH 2.5, and the most preferred active agent green has a pH solution in the range about pH 1.5-about pH 2.0.

Example 4

Phytogenic Friendly Coqui Frog Pesticide

In view of the need to find new phytogenic friendly alternatives for controlling the spread of Coqui frogs, a commercially available food sanitation product (i.e. Acidic Calcium Sulfate ("ACS") was evaluated for inclusion in the current inventory of chemicals that can be applied as sprays. ACS and functional equivalents thereof are made from ingredients that are generally regarded as safe ("GRAS"), and is approved for use in food by the FDA and USDA. Although not wanting to be bound by theory, the efficacy of this product stems from its very unique characteristic of being able to donate a very high activity of hydrogen ions (low pH), while at the same time, having very low oxidative effects on plants and human skin. For example, a five (5) normal concentration of ACS having a pH of approximately zero may be held in the human hand without harm to the person holding the acid. In contrast, when very small amounts are applied to the skin of Coqui frogs it is quickly absorbed and respiration is immediately impaired with lethal results. Results of a field study using one hundred Coqui frogs showed about 95% of all frogs were killed within fifteen minutes when sprayed with as little as 1.0 ml of this an approximate ~11.5% by volume solution of ACS.

Phytotoxicity of the dilute ACS solution used varied from none to moderate, depending on the plant variety and could be minimized depending on the use of a mist versus heavy spray. Most if not all phytotoxic effects could be eliminated by rinsing the plant within thirty minutes following application of the dilute ACS solution. There are many benefits to this product and the balance of frog lethality versus phytotoxicity indicates ACS is a minimal risk pesticide against the Coqui frog infestation.

Commercially available ACS can be utilized as a pH modulator that is a bactericidal GRAS product approved for use in food by the FDA and USDA. It is effective in removing *E-Coli, Salmonella, Listeria, Campylobacter* and other harmful bacteria from food. The platform product is alternately formulated for use with meat, fish, produce, pharmaceuticals and more. The power of this product resides in its very unique characteristic of having both a very high concentration of hydrogen ions (pH of approximately zero at a 5N concentration) while at the same time very low corrosiveness. A 5N concentration of this product having a pH of approximately zero can be held in the palm of one's hand without harm. In contrast, for Coqui frogs, it's another story for when even a very small amount of this low pH product comes into contact with the frogs skin it is quickly absorbed and immediately impacts respiratory function, having lethal effects.

Example 5

Cost Effective Coqui Frog Pesticide

The use of ACS-P has been shown to be a cost-effective and non-toxic means for controlling the spread of Coqui, as determined by a three part field study that was devised to I) determine the lethality of the product on individual frogs and klatches of eggs; II) test the product as a substitute for citric acid in a commercial application; III) apply the product in a residential setting to observe for phytotoxicity and reduction of Coqui noise.

A total of one hundred male and female adult and adolescent Coqui frogs were hand-captured from banana trees in groups of twenty over a five-week period. Upon capture frogs were collectively placed in a large plastic container and then individually moved to 8 oz covered Styrofoam cups, approximately thirty minutes later.

At the bottom of each cup was a 2×2 inch double thickness layer of paper towel saturated with 2 ml of water. Ten minutes after being placed in the cups, each frog was then inoculated with 1.0 ml of an about 11.5% by volume solution of ACS-P in tap water using about 1.0 ml auto-pipette and observed for fifteen minutes. Egg klatches were also recovered from the banana trees and divided into groups of approximately ten each. One group was sprayed with 2 ml of product and one group was untreated. The eggs were observed over two-three weeks.

Except for the largest of the female frogs, about 95% of all frogs expired within a fifteen minutes of inoculation of 1.0 ml of the product. Some of the larger male frogs required an additional ml to cause death within an additional fifteen-minute period whereas many of the smaller adolescent frogs expired almost instantly. Some of the large females that were nearly two inches in length, required inoculation of up to four ml of product before lethality was achieved. It was theorized that these females were more resistant to the product due to higher levels of hydration. It was also determined that once sprayed, affected and/or dead appearing frogs could not be revived by immersing them in water. Most of the untreated eggs hatched whereas none of the treated eggs hatched.

Example 6

Large Scale Field Test of Lethal and Phytotoxicity

Large-scale examples of the product's use and phytotoxicity at the same concentration (about 11.5%) as used in previous examples were also conducted by Palms of Hawaii. A five-gallon back pack sprayer equipped with a mist spray nozzle was used to spray mature Palm trees being prepared for distribution with about a gallon of spray each.

Upon spraying palm trees having frogs, frogs leap off the root balls and crowns and from the junctions between the fronds and tree trunks. The nurseryman rated the complete removal, if not extermination of all frogs from the trees as excellent. He was especially pleased because the ACS-P had no phytotoxic consequences to the trees. Citric acid typically causes browning. Additionally, ants were also driven off the trees.

Following these tests of lethality, tests for phytotoxicity were completed, wherein approximately 500 gallons of ACS-P was applied using a heavy spray nozzle to a ¼ acre yard that is densely covered with various kinds of trees and under growth having a healthy population of Coqui frogs. Plants were observed for phytotoxic effects over a one-week period. Phytotoxicity was found to vary from none to moderate according to the variety of plant. Bromeliads and tender shade-loving plants were found to have yellowed leaves and in some cases brown spots where the spray had made a puddle. More hardy sun-loving plants having thick or waxy leaves were not affected. Additionally, phytotoxic effects can be minimized by using a mist versus heavy spray that doesn't puddle on the leaves, or entirely eliminated by washing the product off the plant with plain water within 30 minutes of application.

In general, the product is designed to come into direct contact with the frog by the spray in order to have lethal effects on the frog. However, surfaces that have accumulated a dried paste of ACS without rinsing or dilution are also lethal to frogs. For example, Styrofoam cups containing dried paste product retained its lethal potential, even after three months.

Using a survey of residents living near the treated field confirmed unanimously that the treated area was noticeably quieter for about 2-3 weeks. Afterwards, it is believed that an existing population of unsprayed frogs in neighboring areas moved into the now frog-free treated area. Rainfall in this area is quite heavy so the effects of the product were assumed to be lost within a few days.

The results of this field study indicate that ACS-P (calcium sulfate saturated with sulfuric acid) produced satisfactory results with frog and noise levels in treated areas. A very desirable quality of this product is that the solution can be easily modified to vary the concentration of hydrogen and calcium ions. An optimal balance of these two elements will result in a solution that is at once lethal to the frogs yet lacking significant phytotoxicity, and may even act as a nutrient to most plants. The solution strength used in this study (e.g. about 11.5% ACS) is the preferred embodiment for a tropical area like Hawaii. However, one skilled in the art will understand that this formulation can be varied and modified to encompass different frogs, flora, and fauna in different Geographic areas around the world. Such modifications of this preferred embodiment is considered to be within the spirit and scope of the application.

Given the efficacy found herein and the fact that ACS-P is made from components generally regarded as safe ("GRAS") and have approval by the FDA and USDA for use in food, ACS-P should be considered for emergency approval by the EPA as a minimal risk pesticide to replace hydrated lime.

Example 7

Phytogenic Friendly Insecticide

The advantages of using superacids as pH adjusters, such as ACS an ACS-P are many. ACS-P is less expensive than citric acid and less hazardous to apply than hydrated lime in combating Coqui frogs. Additionally, these ACS compositions have a number of other potential uses. For example, the lower concentrations and higher pH solutions of ACS can be used as a pesticide for soft-bodied insects and can serve a second use as a plant nutrient to supply calcium via foliar feeding. Additionally, a solution strength having a pH of 1.8, which may be too high to kill some frogs, was effective in killing soft-bodied insects such as aphids and spider mites with minimal phytotoxicity to a Hibiscus plant. At a slightly higher concentration, and when sprayed with approximately 5 ml of product, brown hump back slugs were killed.

In development of the current invention it was also found that ACS alone, or propionic acid having the pH adjusted with ACS also kills tree frogs, cane toads, slugs, including brown or humpback slugs, African snails, nettle and other caterpillars, nematodes, aphids, spider mites, fruit fly larva, and other miscellaneous soft bodied insects that are usually regarded as pests. It also drives off or repels fire ants and termites yet does not appear to harm grasshoppers or lizards. Also immerging on the scene is the honey bee mite known as the Varroa Mite, wherein one drop of this product instantly killed these mites. ACS in water can also inhibit the growth of powdery mildew. When formulated as slurry or suspended in a carrier product such as bentonite clay or vermiculite, this product may be used to form barriers to repel the Coqui frog and other pests. The liquid solution of the product may also be used to inhibit the growth of harmful bacteria such as E-coli, salmonella, and simple rot bacteria present on post-harvest fruit, produce and food preparation surfaces, however the antimicrobial properties for some of the ingredients of this pesticide are clearly established under other patents. The Coqui frog is presently causing the most concern because it is threatening the export of agricultural products from Hawaii to the US Mainland as well as having a stressful impact on the residents and visitors to Hawaii who are in many localities no longer able to experience "Quiet Hawaiian nights," at least without earplugs.

Example 8

Dried Pesticide Retains Killing Efficacy

When a sprayed ACS-P solution is left to dry on a surface, the post-application composition remains lethal to frogs indefinitely and until the product is further diluted or washed away with water. If not killed after coming into contact with this surface residue, frogs will vigorously seek to avoid further contact. One aspect of the lasting lethality of this composition is a product that is useful for forming barriers in nurseries and commercial buildings.

Present manufacturing and distribution costs indicate ACS-P can be made available at wholesale and retail costs that are substantially lower than citric acid. If desired, the product can be used to cut or extend citric acid so as to double the quantity of solution while maintaining equal or lower cost than the original quantity. ACS-P is non-corrosive and at the strengths used in this study, it has no significant hazards to humans or animals.

Given the enormous buffering capacity of earth, there would be negligible risk of ground water contamination from the small amount of post-application runoff that would result from application as a medium or mist spray. A drenching type application using a fire hose nozzle is not required to use this product. The disadvantages of ACS-P are few. Normal eye and face mask protection as typically used in the application of any insecticide should be used when applying this product as minor irritation may occur if the product is allowed to come into contact with the eyes, cuts, or wounds. This irritation would not be any more substantial than that caused by lemon juice and easily relieved by flooding the exposed area with water. Due to the acidity of the concentrated form of this product, it will damage cotton clothing and discolor aluminum and galvanized metal, although still not corrosive to human skin. All in all, it is this author's opinion that this product represents a potentially valuable addition to the present array of products available for combating the spread of Coqui frogs. More such products are urgently needed and this product should be given strong support/consideration for EPA registration as a minimum risk pesticide to replace hydrated lime.

Example 9

Increasing Efficiency by Combining Acid and Salts

An object of the new pesticide product used to the control of Coqui frogs is a combination of different types of acids with other organic/inorganic acids and their respective salts. Previous examples have illustrated how various concentrations of Acidic Calcium Sulfate (ACS-100 or ACS-50) could be used as a low phytotoxic pesticide for Coqui frogs and other soft-bodied species. One of ordinary skill in the art will appreciate that the combinational use of other strong-, weak- and super-acids and salts can be formulated to remain toxic to frogs, but stay environmentally friendly according to EPA guidelines. As such, ACS-100, ACS-50, sulfuric acid, propionic acid, citric acid and/or their respective salts in combination with one or more of the previous mentioned acids is considered to be within the spirit and scope of the invention.

As mentioned in other examples, ACS-P affords an advantage of having compositions capable of forming both a slurry and a dry product, which can be utilized in various types of applications. One disadvantage of a new composition (i.e. ACS-P, ACS-100, or ACS-50), which is unknown to the environmental protection agency ("EPA"), is whether or not its use would be approved quickly enough to stop frog infestations. As such, one aspect of the current invention is to improve the frog killing effects of compounds that are already listed as EPA approved pesticide ingredients, or for frog eradication.

More specifically, compounds such as propionic acid, which are already approved as pesticides, can be used to take advantage of methods described herein to titrate lower pH levels for the purpose of killing frogs, without being as toxic to plants. Propionic acid (systematically named propanoic acid) is a naturally-occurring carboxylic acid with chemical formula $CH_3CH_2COOH$. It is a clear liquid with a pungent odor. The anion $CH_3CH_2COO$ as well as the salts and esters of propionic acid are known as propionates (or propanoates) and are considered to be functional chemical equivalents thereof.

Although not wanting to be bound by current regulations and/or theory, ACS should be formulated to meet the HAZMAT cutoff of pH 2.0, however, titrating ACS with propionic acid or propionic acid salts can be utilized to increase or decrease the pH. In contrast, properly formulated propionic acid is at least as effective as ACS alone in killing frogs, and can be formulated will little effort to have a pH within the HAZMAT regulations of about 2.0. Unfortunately, an increase in concentration may lead to increased phytotoxicity. More specifically, propionic acid is available as a dry product and could be used in much the same way as citric acid is now being used and would cost less per gallon when compared to citric acid. For example, 1 gallon of 16% citric acid costs about $2.40/gallon (retail) and is considered phytotoxic to many plants, whereas, 1 gallon of 16% propionic acid can be formulated to have a lower pH and costs only about $1.00 per gallon with similar or superior phytotoxicity.

Although EPA regulations can present hurdles for entry of new compositions into the pesticide market, citric acid and/or propionic acid are currently products that are on EPAs list 4 and can safely be used in pesticides without concern for non-target species and or negative impact on the water table. As such, modified formulas of citric acid having lower phtotoxicity may also have a lower hurdle for EPA approval. More specifically, it is possible to use ACS in a synergistic way with citric acid to actually lower the 16% concentration that is know to have phytotoxic properties, while retaining the capacity to kill the frogs. For this reason, it may be advantageous to lower the 16% citric acid concentration in order to lower its known phytotoxic effects.

Similarly, a composition of propionic acid is prepared as a liquid using any of the following three methods shown below. The active ingredient is proprionic acid and either ACS or sulfurinc acid is used to adjust the pH downward or one of the propionic salts to adjust the pH upward. ACS-P consists of calcium sulfate saturated with sulfuric acid, can also be used to adjust the pH and/or to make slurry. ACS-P can be dried and/or infused into bentonite clay, vermiculite, or some other functional equivalent carrier capable of making a dry product. All formulations can be made to vary in concentration according to the needs and applications of the user or EPA standards. For example, the pH of the final product solution will for most purposes be at 2.0 or above in order to meet the HAZMAT criteria for non-hazardous products.

Formulation 1. Propionic acid in water.

To make an approximate 10% solution, add about 5-15 ml of propionic acid (90%+purity) to 100 ml of water. Mix and check pH to make sure it falls within the range from 2.0 to 2.5. If pH is greater than 2.5, titrate pH downward by adding a small amount (0.25 to 1.0 ml) of sulfuric acid (90%+purity). If pH is less than 2.0 adjust pH upward using a small amount (+/−about 0.5 to 1.0 gram) of sodium propionate. In a one embodiment, the concentration range of propionic acid is in the range of about 5.0% to about 15%, and the pH is in the range of about 1.5 to about 3.5. In a preferred embodiment, the concentration range of propionic acid is in the range of about 8.0% to about 12.5%, and the pH is in the range of about 1.8 to 2.8. In the most preferred embodiment, the concentration range of propionic acid is in the range of about 9.5% to about 10.5%, and the pH is in the range of about 2.2 to about 2.5. Alternatively, the pH can be titrated for the various concentration ranges using a superacid such as ACS-100, ACS-50, sulfuric acid, hydrochloric acid, or combination thereof (Note: a pipette or syringe can be used to slowly add sulfuric acid for adjusting pH downward to between about pH 2.0 and about pH 2.5. In some instances, it may be unadvisable to allow the total percentage of sulfuric acid used to adjust pH be above about 10% of the total solution, as not to surpass EPA tolerance limit for the use of sulfuric acid as a pH adjuster in pesticides. Additionally, propionic acid is a volatile chemical and may evaporate out of solution within a given period of time. It is therefore advisable to use methods known in the art to prevent such evaporation from occurring. One having ordinary skill in the art will understand that methods and ratios used to industrialize large scale manufacturing protocols of these compositions is included in the spirit and scope of the invention.

Formulation 2. Salt of Propionic Acid in Water.

To make an approximate 10% solution, add about 10 grams of either sodium or calcium propionate to about 100 ml of water, wherein sodium propionate is preferred because it does not leave a precipitant. The initial pH should be in the range of about 4.0 to 6.0. Adjust pH range to about 2.0-about 2.5 using sulfuric acid, ACS-P, ACS-100, or ACS-50. In a one embodiment, the concentration range of the salt of propionic acid is in the range of about 5.0% to about 15%, and the pH is in the range of about 1.5 to about 3.5. In a preferred embodiment, the concentration range of the salt of propionic acid is in the range of about 8.0% to about 12.5%, and the pH is in the range of about 1.8 to about 2.8. In the most preferred embodiment, the concentration range of the salt of propionic acid is in the range of about 9.5% to about 10.5%, and the pH is in the range of about 2.2 to about 2.5. Alternatively, the pH can be titrated for the various concentration ranges using a superacid, ACS-100, ACS-50, sulfuric acid, or hydrochloric acid. One having ordinary skill in the art will understand that methods and ratios used to industrialize large scale manufacturing protocols of these compositions is included in the spirit and scope of the invention.

Formulation 3. Acs-P and Acs-100 in Water.

ACS-P and ACS 100 in water with or without the use of any other ingredients to adjust the pH of the solution, in one embodiment of this invention, an approximate 10% solution can be made by adding about 10 grams of ACS-P 50 to 100 ml of tap water and mix thoroughly. The pH should be should be in the range of about pH 1.1 to about pH 1.3. The pH can be adjusted within the desired range of about pH 1.0 by adding a few ml of ACS. If the pH adjustment results in a pH that is below 1.0, a small amount of calcium hydroxide can be added to increase the pH. The clear liquid can be decanted from any precipitant; the decanted liquid can be used as a spray. Save the white precipitant created in this process for use as a slurry product as described in Formulation 4 described below.

Since, the pH of this solution is about pH 1.0, it may harm certain plants by turning the leaves yellow, wherein most plants should recover and plants should not die from application of this product. Although not wanting to be bound by theory, this product should be maintained in a range between about pH 0.5 to about pH 2.0. In a preferred embodiment, the pH range should be between about pH 0.9 and about pH 1.5. In the most preferred embodiment, the pH range should be about pH 1.0 to about pH 1.3 in order to remain effective at killing frogs. Additionally, to be effective, about 1 ml of this product should come into direct contact with the frog. Although not wanting to be bound by theory, more than about 1 ml of product may be needed to kill larger female frogs since they may withstand and may be capable of neutralizing the product due to females being more highly hydrated than male frogs. Although not wanting to be bound by theory, female frogs may retain more water in their bodies in order to keep their eggs hydrated. One having ordinary skill in the art will understand that methods and ratios used to industrialize large scale manufacturing protocols for these compositions is included in the spirit and scope of the invention. (Note: By adding a sticker that is normally used in pesticides to any of the above solutions in the manner known by one of ordinary skill in the art of sticker products, the efficacy of this pesticide product may be improved by the reduction in surface tension brought about as a result of adding the sticker.)

Formulation 4. Acs in Combination with Citric Acid.

Citric acid is currently the only substance approved by the Hawaii Department of Agriculture (HDOA) for use against Coqui frogs. Although not wanting to be bound by theory, ACS can be used to extend and potentiate citric acid and make a solution that is equally if not more effective at a cheaper price. In one embodiment, about 14 grams of citric acid can be added to about 10 ml ACS 100 or about 10 ml of sulfuric acid or about 18 grams of ACS-P 50 and about 200 ml of water. The pH of this solution can be increased to about pH 2.0 by adding sodium propionate. In a preferred embodiment, the concentration range of the citric acid is in the range of about 5.0% to about 20%, and the pH is in the range of about 1.0 to about 3.0. In the most preferred embodiment, the concentration range of the salt of propionic acid is in the range of about 9.5% to about 10.5%, and the pH is in the range of about pH 1.8 to about pH 2.2. Alternatively, the pH can be titrated for the various concentration ranges using a superacid, ACS-100, ACS-50, sulfuric acid, or hydrochloric acid. One having ordinary skill in the art will understand that methods and ratios used to industrialize large scale manufacturing protocols of these compositions is included in the spirit and scope of the invention.

Formulation 5. The Product as Slurry.

The product as slurry may be useful for painting onto surfaces that are designed to serve as a barrier to the frogs, snails, nematodes, or other soft-bodied invertebrates. Although not wanting to be bound by theory, these soft-bodied creatures will not cross a barrier containing the slurry and may be killed after contacting it. The slurry can be saturated into a piece of loosely woven cloth or painted on a flat surface. Cloth saturated with slurry can be wrapped around a tree trunk, plant stem, or applied to a flat surface.

One simple way to make a slurry product is to reuse the precipitant from Formulation 3 from above, or by adding a small amount of water to the ACS-P sludge obtained from the Mionix ACS production factory. The final pH of the slurry should be in the range of above zero and about pH 1.0. Although not wanting to be bound by theory, the precipitant from Formulation 3 above will have a higher than desired pH, wherein a small amount of ACS 100 or sulfuric acid will need to be added to lower the pH to the desired level. Although the solutions produced in Formulation 1, and Formulation 2 above can be made into slurry by adding about ten (10) to about twenty (20) grams of calcium carbonate, there may be no need to do this when ACS-P is readily available. One having ordinary skill in the art will understand that methods and ratios used to industrialize large scale manufacturing protocols of these compositions is included in the spirit and scope of the invention.

Formulation 6. The Dry Product. Drying the ACS-P and then processing the dried product to a desired size or by adding the liquid or slurry to a carrier such as a bentonite clay, vermiculite, lava cinder, or other inert suitable ingredient can make a dry product. Although not wanting to be bound by theory, the adsorbed or absorbed acids of this invention is believed to be available from the acidified clay as a residual pesticide capable of killing the frogs. The clays or minerals suitable for this invention include montmorillonite clay, phyllosilicate, Florisil®, bayerite, pseudoboehmite, alumina, silica gel, aluminum oxides, gibbsite, boehmite, and bauxite. Other compounds capable of absorbing and releasing the acids are also considered to be within the spirit and scope of the invention. Similar to the slurry, the dry product has residual effects and can be used as a barrier for application to the surface soil of potted plants, around the base of trees, or to make a perimeter defense zone in a nursery or other area that is protected from rain or irrigation water. The slurry product can also be used in this same manner.

Although not wanting to be bound by theory, a dry product is made using one of the liquid products above and adding about one (1) to two (2) parts of liquid solution to about four (4) parts carrier product, mix to form a thick slurry allow to dry. After drying process the dried product to the desired particle size and apply to the surface soil of potted plants or spread around the area where a barrier to the frogs is desired. In some instances, it may be appropriate to add a barrier to prevent the potted plant from the low pH product that could leach down into the potting soil. Although not wanting to be bound by theory, if the low pH product leaches down into the soil as a result of it coming into contact with irrigation water, the pH of the potting soil could be reduced to the point that it harms the plant, even if only temporarily. For example, one may use a piece plastic to cover the dry product soil and keep it separated from the potting soil. Namely, a piece of plastic in the range of about 3 mm to about 9 mm thick, however, one having ordinary skill in the art will understand that methods and ratios used to utilize barriers made from functional equivalents of plastic for preventing cross reactivity from these compositions and areas that need to be protected from these compositions, and are included in the spirit and scope of the invention.

Example 10

Frog Killing Time with Different Concentrations

The efficacy of a properly formulated solution of ACS-P fortified with ACS 100 having a final pH of about pH 1.0, was found to have a similar killing efficiency as hydrated lime. Additionally, this formulation killed 10 out of 10 frogs within about 15 minutes. More over, concentrations using proprionic acid ranging from about 5% to about 10% were lethal to the frogs in the test group. It was found that the 10% solution of proprionic acid killed frogs faster than standard citric acid and the 5% proprionic acid killed equally fast, whereas the ACS-P alone took the longest time to kill the frogs.

Example 11

Composition and Method for Killing Frogs

One aspect of this invention is an acidic aqueous pesticide composition for killing a soft-bodied animal (e.g. a Coqui frog; a Coqui frog egg; a tree frog, a cane toad, a slug, a nettle, a caterpillar, a nematode, an aphid, a spider mite, fruit fly larva, a varro mite and other soft bodied insects that are usually regarded as pests, or a combination thereof). The acidic aqueous pesticide composition comprises: an organic acid solution having concentration below 16% (w/v) as a percentage of the aqueous pesticide composition; and a pH for the acidic aqueous pesticide below pH 3.0, wherein, the organic acid is selected from: a citric acid, a propionic acid, or a mixture thereof. The acidic aqueous pesticide composition can be further defined as comprising an acidic calcium sulfate (ACS) solution having a concentration below 20% (w/v) as a percentage of the aqueous pesticide composition. The acidic aqueous pesticide composition of can further be formulated to comprise a sulfuric acid solution having a concentration below 10% (w/v) as a percentage of the aqueous pesticide composition. Additionally, the aqueous pesticide composition may further comprise a surfactant for the surface area of the aqueous pesticide composition on the soft bodied animal of interest wherein the surfactant is selected from: an ionic-, anionic-, zwitterionic-surfactant, or combination thereof.

In a particular embodiment, the acidic aqueous pesticide composition comprises the organic acid concentration having a range of 5% to 15% (w/v); the ACS solution having a concentration of below about 20% (w/v); the sulfuric acid solution having a concentration about 0% (w/v); the acidic aqueous pesticide composition having a pH in the range of pH 0.8 to pH 2.5. In a second particular embodiment, the acidic aqueous pesticide composition of claim 3, wherein, the organic acid concentration having a range of 8% to 12% (w/v); the ACS solution having a concentration of below 20% (w/v); the sulfuric acid solution having a concentration about 0% (w/v); and the acidic aqueous pesticide composition having a pH in the range of pH 1.0 to pH 2.0. In a third particular embodiment, the acidic aqueous pesticide composition of claim 3, wherein, the organic acid concentration is about 12% (w/v); the ACS solution having a concentration of about 20% (w/v); the sulfuric acid solution having a concentration below 0% (w/v); and the acidic aqueous pesticide composition having a pH of about pH 1.5; and the soft-bodied animal is selected from: a Coqui frog; a Coqui frog egg. In a fourth particular embodiment, the acidic aqueous pesticide composition comprises the organic acid concentration having a range of 5% to 15% (w/v); the ACS solution having a concentration of about 0% (w/v); the sulfuric acid solution having a concentration below about 10% (w/v); the acidic aqueous pesticide composition having a pH in the range of pH 0.8 to pH 2.5. In a fifth particular embodiment, the acidic aqueous pesticide composition comprises the organic acid concentration having a range of 8% to 12% (w/v); the ACS solution having a concentration of about 0% (w/v); the sulfuric acid solution having a concentration below about 10% (w/v); and the acidic aqueous pesticide composition having a pH in the range of pH 1.0 to pH 2.0. In a sixth particular embodiment, the acidic aqueous pesticide composition comprises the organic acid concentration having about 12% (w/v); the ACS solution having a concentration of about 0% (w/v); the sulfuric acid solution having a concentration below 10% (w/v); and the acidic aqueous pesticide composition having a pH of about pH 1.5; and the soft-bodied animal is selected from: a mature Coqui frog; a Coqui frog egg; or a juvenile Coqui frog.

In an advantageous embodiment, a method of killing a soft-bodied animal of interest with an acidic pesticide composition is disclosed. The method comprising the steps of: Step 1: locating the soft-bodied animal or locating an area where the soft-bodied animal resides; Step 2: contacting the soft-bodied animal with the acidic pesticide composition; wherein, the acidic pesticide composition comprises: an acidic calcium sulfate (ACS) solution having a concentration of below about 20% (w/v); the acidic pesticide composition having a pH in the range of pH 0.8 to pH 2.5; and the acidic pesticide composition is a liquid or a solid form; wherein, and the soft-bodied animal is selected from: a Coqui frog; a Coqui frog egg; a tree frog, a cane toad, a slug, a nettle, a caterpillar, a nematode, an aphid, a spider mite, fruit fly larva, a varro mite and other soft bodied insects that are usually regarded as pests, or a combination thereof.

In an advantageous embodiment, a method of killing a soft-bodied animal of interest with an acidic aqueous pesticide composition, the method comprising the steps of: Step 1: locating the soft-bodied animal or locating an area where the soft-bodied animal resides; Step 1.1: placing a lure in the area inhabited by the soft-bodied animals of interest, wherein placing the lure occurs prior to the method step (1.2) of spraying the acidic aqueous pesticide and the lure remains in the area indefinitely; Step 1.2: spraying the acidic aqueous pesticide composition in the area inhabited by the soft bodied animals of interest, wherein, spraying the acidic aqueous pesticide composition occurs prior to the method step (2) of contacting the soft bodied animal of interest; Step 2: contacting the soft-bodied animal with the acidic aqueous pesticide composition; wherein, the acidic aqueous pesticide composition comprises: an organic acid solution having concentration below 16% (w/v) as a percentage of the aqueous pesticide composition; and a pH for the acidic aqueous pesticide below pH 3.0; wherein, the organic acid is selected from: a citric acid, a propionic acid, or a mixture thereof; and the soft-bodied animal is selected from: a Coqui frog; a Coqui frog egg; a tree frog, a cane toad, a slug, a nettle, a caterpillar, a nematode, an aphid, a spider mite, fruit fly larva, a varro mite and other soft bodied insects that are usually regarded as pests, or a combination thereof; Step 3: waiting a period of time; wherein the period of time is in a range of 2 days to about 10 days. Step 3.1: checking the lure after the period of time; Step 3.2: discarding any Coqui frogs or Coqui frog eggs found in the lure. Step 4: repeating the method from step 1 until the area inhabited by the soft-bodied animals has a significantly reduced number of soft-bodied animals of interest. The method of this invention uses a means for spraying the acidic aqueous pesticide composition in the area inhabited by the soft bodied animals of interest is selected from: a hand sprayer; a garden sprayer with volumes less than about 10 liters; Mounted Sprayer-Semi Hydraulic; Trailed Sprayer; Mounted Sprayer With Hydraulic Boom; Trailed Sprayer With High Wheel; Trailed Sprayer High Wheel With Electronic Control Unit; Mounted Sprayer-Basic Type; Mounted Sprayer-Basic Type With Clean Water Tank; Garden Sprayer; High Pressure Diaphragm Pump; Power Sprayer With Electric or Fuel Powered Engine; Fertilizer Spreader; Interrow Rotary Cultivator; or a functional equivalent thereof. One of ordinary skill in the art will understand there are many methods for spraying a liquid on a plant that are not listed here, but are contained within the sprit and scope of this invention.

Example 12

Apparatus and Method for Killing Frogs on Plants

Figure 1:
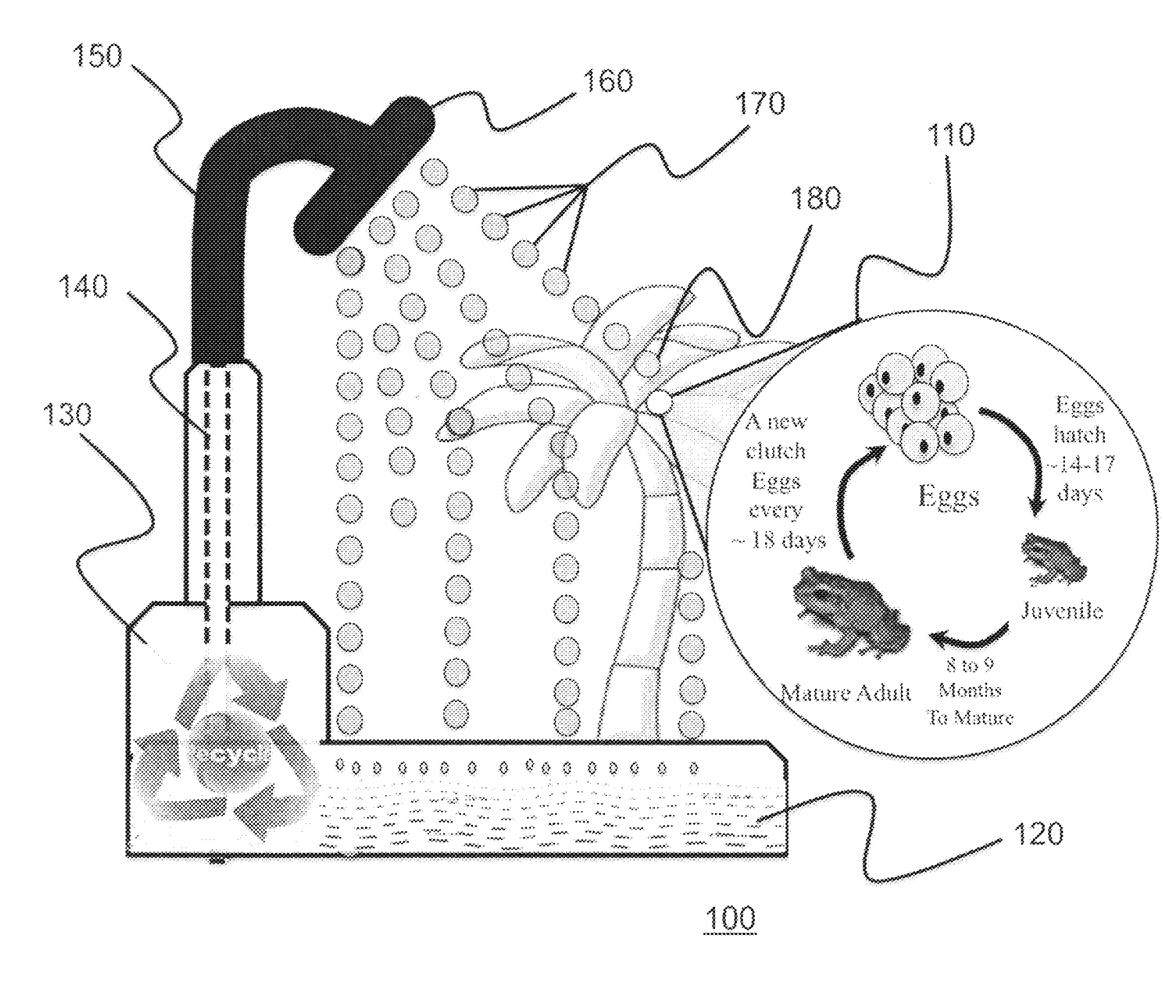
FIG. 1 shows an apparatus and method for killing frogs, and frog eggs on plants that will be either imported or exported.

Although not wanting to be bound by theory, pNow referring to FIG. 1 in this application, a general pesticide recycling system for treating plants of interest that are imported or exported from exotic locations having the potential for infestation with an invasive species 100. This system is shown comprising an invasive species life cycle 110, a acidic pesticide recapture tank 120, a filter 125, an acidic acid transfer and/or recycling pump. Typical fluid recycle lines are interconnected among the various components of the system with, for example, the inlet side of the outlet transfer line 140 connected to the outlet of the transfer or recycle pump 130. As the pesticide is pumped through the sprayer line 150 into the sprayer head 160, the pesticide is transitioned into droplets 170 that shower the plants of interest 180, which are sitting on acidic pesticide recapture tank 120. Not depicted in FIG. 1 but understood as comprising a part of the pesticide recycling system, are power or air pressure lines supplying power to spray the pesticide onto the plants of interest.

In summary, the Coqui frog population has become a serious problem in some parts of the world. The previous methods for irradiating or controlling the frog population have been shown to be either uneconomical, restricted in scope or not environmentally friendly. The related art has shown that it is possible to impact frog populations in a limited capacity by utilizing physical means such as collection tubes; lures; and traps. In contrast, chemical methods of frog eradication have shown better success than physical means (e.g. caffeine, pyrenone, and citric acid solutions), however, these compounds may have a prolonged phytotoxic damage that impacts the entire ecosystem in heavily treated areas. There is a need in the art for an expanded environmentally and phyoloycially friendly composition and methods of treating small and large areas of Coqui frog infestations.

This pesticide can be made or produced in a variety of wet and dry products and in varying concentrations. These include: 1) the dilution of the active ingredient in its commercially available form with or without the use of other ingredients to adjust the final pH of the solution. Possible active ingredients include but are not limited to propionic acid, lactic citric acid, lactic acid, and vinegar; 2) the dilution of the salts of the active ingredients listed in (1) in water with the addition of an acidulant to reactivate the active organic acid ingredient and to adjust the final pH. Possible acidulants include but are not limited to acidic calcium sulfate, sulfuric acid, and hydrochloric acid; 3) the dilution of ACS 100 or it's by-product ACS-P 50 in water with or without the use of any other ingredients to adjust the pH of the solution; 4) preparation of slurry using any one of the products listed in 1-3 above. Additional inert ingredients such as calcium carbonate or calcium hydroxide may be use to provide a calcium base to increase the viscosity of the slurry; 5) combining any of the ingredients as listed above with a sticker used in pesticides or other inert carrier product such as a bentonite clay, vermiculite, lava cinder or other inert suitable ingredient to create a wet or dry product with residual effects. The innovative use of highly diluted propionic acid as it commercially produced or is regenerated by using ACS or sulfuric acid in conjunction with sodium or calcium propionate produces a highly effective pesticide for the control of the Coqui frog and other invasive species named herein. It is not hazardous to humans or animals and is minimally phytotoxic. The EPA has no residual tolerance limitations for propionic acid or its salts when used as active ingredients in pesticides, and approves up to a ten percent solution of sulfuric acid may be added to pesticides to adjust pH. No harmful effects on the environment or birds and animals are anticipated from use of this pesticide. Ninety percent or above purity of propionic acid may be used in water without a pH adjustor but is more corrosive than when used with ACS-P 50 or ACS 100 as a pH adjustor. The solution strength recommended herein has a minimum phytotoxicity for most plants (none if washed off within thirty minutes of application) and the added calcium (350 ppm) actually serves as a plant nutrient. As a highly diluted solution of food grade chemicals that are generally regarded as safe, this pesticide will have negligible risk to humans, pets, farm animals, material products such as sprayers, or the environment. ACS alone is used in the drinking water of chickens and when combined with chlorine forms a highly effective vegetable wash (These are previously patented uses by other entities). Once these two chemicals come into contact with the ground the low pH (2.0-4.0) is quickly neutralized by the earth and/or surface water or ground water leaving only calcium or calcium sulfate, both regarded as soil amendments. At present there are no other products available that have comparable efficacy, safety, and cost-effectiveness. Due to the fact all the ingredients of this pesticide are GRAS and approve for use in food, this inventor concludes that the new compound formed by the combination of these substances should also be regarded as GRAS and therefore qualify as a minimum risk pesticide for the purposes described herein. Approval by the EPA will be pursued under the protection of the non-provisional patent to be issued under this application.

REFERENCES CITED

The entire content of each of the following U.S. patent documents and published references are hereby incorporated by reference.

U.S. Patent Documents

1. U.S. Pat. No. 7,323,436 titled: "Adduct having an acidic solution of sparingly-soluble group HA complexes," issued to Kemp et al., on Jan. 29, 2008.
2. U.S. Pat. No. 6,902,753 titled: "Acidic solution of sparingly-soluble group HA complexes," issued to Kemp et al., on Jun. 7, 2005.
3. U.S. Pat. No. 6,881,424 titled: "Highly acidic metalated organic acid," issued to Kemp et al., on Apr. 19, 2005.
4. U.S. Pat. No. 6,808,730 titled: "Highly acidic metalated organic acid as a food additive," issued to Kemp et al., on Oct. 26, 2004.
5. U.S. Pat. No. 6,572,908 titled: "Highly acidic metalated organic acid as a food additive," issued to Kemp et al., on Jun. 3, 2003.
6. U.S. Pat. No. 6,436,891 titled: "Adduct having an acidic solution of sparingly-soluble group HA complexes," issued to Kemp et al., on Aug. 20, 2002.

Homeowner's guide to Stopping the spread of Coqui Frogs on Maui, MAUI invasive Species Committee, Paia, Hi. May 2003.

Product Safety Assessment Data Sheet of Propionic Acid, From Dow Chemical, printed, 2008.

MSDS for propionic Acid, From BASF.

MSDS for ACS 50, from Mionix Corporation

MSDS for ACS 100 from Mionix Corporation

MSDS for Diluted ACS 50, from Mionix Corporation

What is claimed is:

1. A method of killing a soft-bodied animal with an acidic pesticide composition, the method comprising the steps of:

Step 1: locating the soft-bodied animal or locating an area where the soft-bodied animal resides;

Step 2: contacting the soft-bodied animal with the acidic aqueous pesticide composition;

wherein, the acidic pesticide composition comprises:

an acidic calcium sulfate (ACS) solution having sparingly-soluble Group IIA complexes prepared by mixing a mineral acid and a Group IIA hydroxide, a Group IIA salt of a dibasic acid, or a mixture of the Group IIA hydroxide and Group IIA salt followed by removing the solid formed; and diluting the ACS solution concentration to a pH in the range of pH 0.8 to pH 2.5 forming the acidic pesticide composition;

wherein, and the soft-bodied animal is selected from: a Coqui frog; a Coqui frog ego; a tree frog, a cane toad, a slug, a nettle, a caterpillar, a nematode, an aphid, a spider mite, fruit fly larva, a varro mite, or a combination thereof.

2. A method of killing a soft-bodied animal with an acidic aqueous pesticide composition, the method comprising the steps of:

Step 1: locating the soft-bodied animal or locating an area where the soft-bodied animal resides;

Step 2: contacting the soft-bodied animal with the acidic aqueous pesticide composition or residue thereof;

wherein, the acidic aqueous pesticide composition comprises:
(a) an acidic calcium sulfate (ACS) solution having sparingly-soluble Group IIA. complexes, ACS having a concentration between 5% and 25% (w/v) as a percentage of the aqueous pesticide composition; and
(b) an organic acid solution having concentration range of 5% to 20% (w/v) as a percentage of the aqueous pesticide composition,
(c) a pH for the acidic aqueous pesticide below pH 3.0;
wherein, the acidic calcium sulfate (ACS) solution of sparingly-soluble Group IIA complexes is prepared by mixing a mineral acid and a Group IIA hydroxide, a Group IIA salt of a dibasic acid, or a mixture of the Group IIA hydroxide and Group IIA salt followed by removing the solid formed;
wherein, the ACS has an acidic pH value and an acid normality value, wherein the ACS is less corrosive to a ferrous metal than is a solution of a mineral acid having the same acidic pH value as that of the ACS, and wherein the ACS is more biocidal than a mixture of the organic acid and a metal salt of the organic acid which mixture having the same acid normality value as that of the ACS; and the organic acid is citric acid, propionic acid or mixture thereof;
wherein, and the soft-bodied animal is selected from: a Coqui frog; a Coqui frog egg; a tree frog, a cane wad, a slug, a nettle, a caterpillar, a nematode, an aphid, a spider mite, fruit fly larva, a varro mite, or a combination thereof.

3. The method of claim 2, further comprising the steps of:
Step 1.2: spraying the acidic aqueous pesticide composition in the area inhabited by the soft bodied animals, wherein, spraying the acidic aqueous pesticide composition occurs prior to the method step (2) of contacting the soft bodied animal with the acidic aqueous pesticide composition;
Step 3: waiting a period of time; wherein the period of time is in a range of 2 days to about 10 days.
Step 4: repeating the method from Step 1 until the area inhabited by the soft-bodied animals has a significantly reduced number of soft-bodied animals of interest.

4. The method of claim 3, further comprising the steps of:
Step 1.1: placing a lure in the area inhabited by the soft-bodied animals, wherein placing the lure occurs prior to the method step (2) of spraying the acidic aqueous pesticide and the lure remains in the area indefinitely;
Step 3.1: checking the lure after the period of time;
Step 3.2: discarding any Coqui frogs or Coqui frog eggs found in the lure.

5. The method of claim 3, wherein, a means for spraying the acidic aqueous pesticide composition in the area inhabited by the soft, bodied animals is selected from: a hand sprayer; a garden sprayer with volumes less than about 10 liters; Mounted Sprayer-Semi Hydraulic; Trailed Sprayer; Mounted Sprayer With Hydraulic Boom; Trailed Sprayer With High Wheel; Trailed Sprayer High Wheel With Electronic Control Unit; Mounted Sprayer-Basic Type; Mounted Sprayer-Basic Type With Clean Water Tank; Garden Sprayer; High Pressure Diaphragm Pump; Power Sprayer With Electric or Fuel Powered Engine; Fertilizer Spreader; Interrow Rotary Cultivator; or a functional equivalent thereof.

6. A method of killing a soft-bodied animal with an acidic pesticide composition residue, the method comprising the steps of:

Step 1: locating an area where the soft-bodied animal may touch;

Step 2: contacting the area with the acidic pesticide composition residue;

Step 3: allowing the acidic pesticide composition to dry leaving the residue;

Step 4: permitting the soft-bodied animal to contact the residue;

wherein, the acidic pesticide composition comprises:
(a) an acidic calcium sulfate (ACS) solution having sparingly-soluble Group IIA complexes, ACS having a concentration between 5% and 25% (w/v) as a percentage of the aqueous pesticide composition; and
(b) an organic acid solution having concentration range of 5% to 20% (w/v) as a percentage of the aqueous pesticide composition,
(c) a pH for the acidic aqueous pesticide below pH 3.0;
wherein, the acidic calcium sulfate (ACS) solution of sparingly-soluble Group IIA complexes is prepared by mixing a mineral acid and a Group IIA hydroxide, a Group IIA salt of a dibasic acid, era mixture of the Group IIA hydroxide and Group IIA salt followed by removing the solid formed;
wherein, the ACS has an acidic pH value and an acid normality value, wherein the ACS is less corrosive to a ferrous metal than is a solution of a mineral acid having the same acidic pH value as that of the ACS, and wherein the ACS is more biocidal than a mixture of the organic acid and a metal salt of the organic acid which mixture having the same acid normality value as that of the ACS; and the organic acid is citric acid, propionic acid or mixture thereof;
wherein, and the soft-bodied animal is selected from: a Coqui frog; a Coqui frog egg; a tree frog, a cane toad, a slug, a nettle, a caterpillar, a nematode, an aphid, a spider mite, fruit fly larva, a varro mite; or a combination thereof.

* * * * *